(12) United States Patent
Yamagata et al.

(10) Patent No.: US 11,331,072 B2
(45) Date of Patent: May 17, 2022

(54) ULTRASOUND MEDICAL DEVICE AND ULTRASOUND DIAGNOSTIC IMAGING DEVICE

(71) Applicant: TOSHIBA MEDICAL SYSTEMS CORPORATION, Otawara (JP)

(72) Inventors: Hitoshi Yamagata, Otawara (JP); Makoto Hirama, Otawara (JP)

(73) Assignee: Canon Medical Systems Corporation, Otawara (JP)

(*) Notice: Subject to any disclaimer, the term of this patent is extended or adjusted under 35 U.S.C. 154(b) by 2005 days.

(21) Appl. No.: 14/290,000

(22) Filed: May 29, 2014

(65) Prior Publication Data

US 2014/0276079 A1 Sep. 18, 2014

Related U.S. Application Data

(63) Continuation of application No. PCT/JP2013/077175, filed on Oct. 4, 2013.

(30) Foreign Application Priority Data

Oct. 4, 2012 (JP) .............................. JP2012-222588

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/0883* (2013.01); *A61B 8/445* (2013.01); *A61B 8/4494* (2013.01);
(Continued)

(58) Field of Classification Search
CPC ....... A61B 8/12; A61B 1/041; A61B 17/2202; A61B 1/00101; A61B 8/4472; A61B 8/42;
(Continued)

(56) References Cited

U.S. PATENT DOCUMENTS

| 4,936,307 A | 6/1990 | Saito et al. |
| 5,313,950 A * | 5/1994 | Ishikawa .................. A61B 8/12 |
| | | 600/459 |

(Continued)

FOREIGN PATENT DOCUMENTS

| CN | 1455655 A | 11/2003 |
| CN | 101384921 A | 3/2009 |

(Continued)

OTHER PUBLICATIONS

International Search Report dated Oct. 29, 2013 for PCT/JP2013/077175 Filed on Oct. 4, 2013 with English Translation.

(Continued)

*Primary Examiner* — Angela M Hoffa
(74) *Attorney, Agent, or Firm* — Oblon, McClelland, Maier & Neustadt, L.L.P.

(57) ABSTRACT

An ultrasound medical device and an ultrasound diagnostic imaging device are provided that allow orally-fed fluid food, etc. to pass through the esophagus of the subject. The ultrasound medical device includes a capsule-type main body configured to incorporate ultrasound transducers, so that the ultrasound transducers in the capsule-type main body, which has been inserted in a tubular body part of a subject, send ultrasound waves to the subject's interiors and receive reflected waves. The ultrasound medical device further includes a support configured to be incorporated in the capsule-type main body and to have a form of tube with (Continued)

a through-hole axially passing through the tube. The ultrasound transducers are arranged external to the tube.

15 Claims, 27 Drawing Sheets

(51) Int. Cl.
*A61B 8/08* (2006.01)
*B06B 1/06* (2006.01)
*B06B 1/02* (2006.01)
*G01S 7/52* (2006.01)

(52) U.S. Cl.
CPC .......... *B06B 1/0215* (2013.01); *B06B 1/0633* (2013.01); *B06B 2201/76* (2013.01); *G01S 7/5208* (2013.01)

(58) Field of Classification Search
CPC .......... A61B 8/44; A61B 8/4444–4494; A61B 8/0883; A61B 5/6861; A61B 2562/162; A61B 5/687
See application file for complete search history.

(56) References Cited

U.S. PATENT DOCUMENTS

| | | | |
|---|---|---|---|
| 6,585,641 B1 | 7/2003 | Jordfald | |
| 7,578,788 B2* | 8/2009 | Yokoi | A61B 1/00087 600/109 |
| 8,512,219 B2* | 8/2013 | Ferren | A61B 1/00156 600/12 |
| 8,923,949 B2* | 12/2014 | Amit | A61B 1/00082 600/424 |
| 9,801,527 B2* | 10/2017 | Ferren | A61B 1/00156 |
| 9,968,290 B2* | 5/2018 | Belson | A61B 1/00158 |
| 10,123,771 B2* | 11/2018 | Asahina | A61B 8/12 |
| 2002/0065512 A1 | 5/2002 | Fjield et al. | |
| 2005/0033166 A1 | 2/2005 | Hastings et al. | |
| 2005/0182342 A1* | 8/2005 | Dinsmoor | A61B 5/073 600/593 |
| 2008/0103440 A1* | 5/2008 | Ferren | A61B 1/00156 604/95.01 |
| 2008/0161639 A1 | 7/2008 | Katayama et al. | |
| 2009/0005639 A1 | 1/2009 | Kawano et al. | |
| 2009/0270736 A1* | 10/2009 | Miyamoto | A61B 8/12 600/462 |
| 2011/0034809 A1* | 2/2011 | Eberle | B06B 1/0633 600/467 |
| 2012/0022375 A1* | 1/2012 | Deladi | G10K 11/30 600/443 |
| 2012/0150024 A1 | 6/2012 | Amit et al. | |
| 2015/0025384 A1* | 1/2015 | Asahina | A61B 8/12 600/443 |
| 2015/0051450 A1* | 2/2015 | Mittal | A61B 5/0261 600/301 |

FOREIGN PATENT DOCUMENTS

| | | |
|---|---|---|
| CN | 101573070 A | 11/2009 |
| JP | 58-118738 A | 7/1983 |
| JP | 1-141652 A | 6/1989 |
| JP | 2-224650 A | 9/1990 |
| JP | 5-92003 A | 4/1993 |
| JP | 5-244694 A | 9/1993 |
| JP | 2002-159495 A | 6/2002 |
| JP | 2005-27724 A | 2/2005 |
| JP | 2005-176907 A | 7/2005 |
| JP | 2006-13016 A | 1/2006 |
| JP | 2006-141574 A | 6/2006 |
| JP | 2008-183278 A | 8/2008 |
| JP | 2012-005837 A | 1/2012 |

OTHER PUBLICATIONS

Combined Office Action and Search Report dated Jun. 3, 2015 in Chinese Patent Application No. 201380006377.1 (with English Translation of Category of Cited Documents).
Combined Office Action and Search Report dated Dec. 11, 2015 in Chinese Patent Application No. 201380006377.1 with English translation of category of cited documents.
Office Action dated Aug. 30, 2016 in Japanese Patent Application No. 2012-222588.

* cited by examiner

ULTRASOUND MEDICAL DEVICE AND ULTRASOUND DIAGNOSTIC IMAGING DEVICE

CROSS-REFERENCE TO RELATED APPLICATION

This application is based upon and claims the benefit of priority from Japanese Patent Applications No. 2012-222588 filed on Oct. 4, 2012; the entire contents of which are incorporated herein by reference.

FIELD

Embodiments relate to ultrasound medical devices and ultrasound diagnostic imaging devices.

BACKGROUND

Ultrasound diagnostic imaging devices are used together with ultrasound probes to scan a subject by ultrasound and to generate images of internal body parts of the subject, based on data acquired from the reflected waves.

An example of such ultrasound probes used with ultrasound diagnostic imaging devices is a TEE (trans-esophageal echocardiography) probe (e.g., see patent reference 1). The TEE probe is, for example, orally inserted into the esophagus for scanning the heart, etc. The TEE probe comprises a guiding hollow tube, which is inserted into the esophagus, and an insert provided at the leading end of the guiding hollow tube.

Passed through the guiding hollow tube, are a power line for sending electrical power to ultrasound transducers, a control line for sending control signals to the ultrasound transducers, and a data line for transmitting data from the ultrasound transducers.

The ultrasound transducers are disposed at the tip of the insert. While the interiors of the subject are being scanned and observed by ultrasound, the insert is kept in contact with the inner wall of the esophagus.

There are requests for realization of postoperative long-term observation of the heart, etc., and in such cases, the above-mentioned insert should be constructed in a capsule type and be maintained in the esophagus for a long period of time.

During a long-term observation, however, the subject needs to be fed with fluid food, water, etc. or be inserted into the esophagus with a trans-nasal endoscope. Hereinafter, such fluid food, water, and trans-nasal endoscope may be collectively referred to as "fluid food, etc."

DETAILED DESCRIPTION

The present embodiments are to solve the above-mentioned problem, and their objective is to provide an ultrasound medical device and an ultrasound diagnostic imaging device that allow orally-fed fluid food, etc. to pass through the esophagus of the subject.

An ultrasound medical device of the embodiment comprises a capsule-type main body configured to incorporate ultrasound transducers, so that the ultrasound transducers in the capsule-type main body, which has been inserted in a tubular body part of a subject, send ultrasound waves to the subject's interiors and receive reflected waves. The ultrasound medical device further comprises a support configured to be incorporated in the capsule-type main body and to have a form of tube with a through-hole axially passing through the tube, and the ultrasound transducers are arranged external to the tube.

First Embodiment

Now, a first embodiment of ultrasound diagnostic imaging device is described with reference to each of the drawings.

Figure 1:
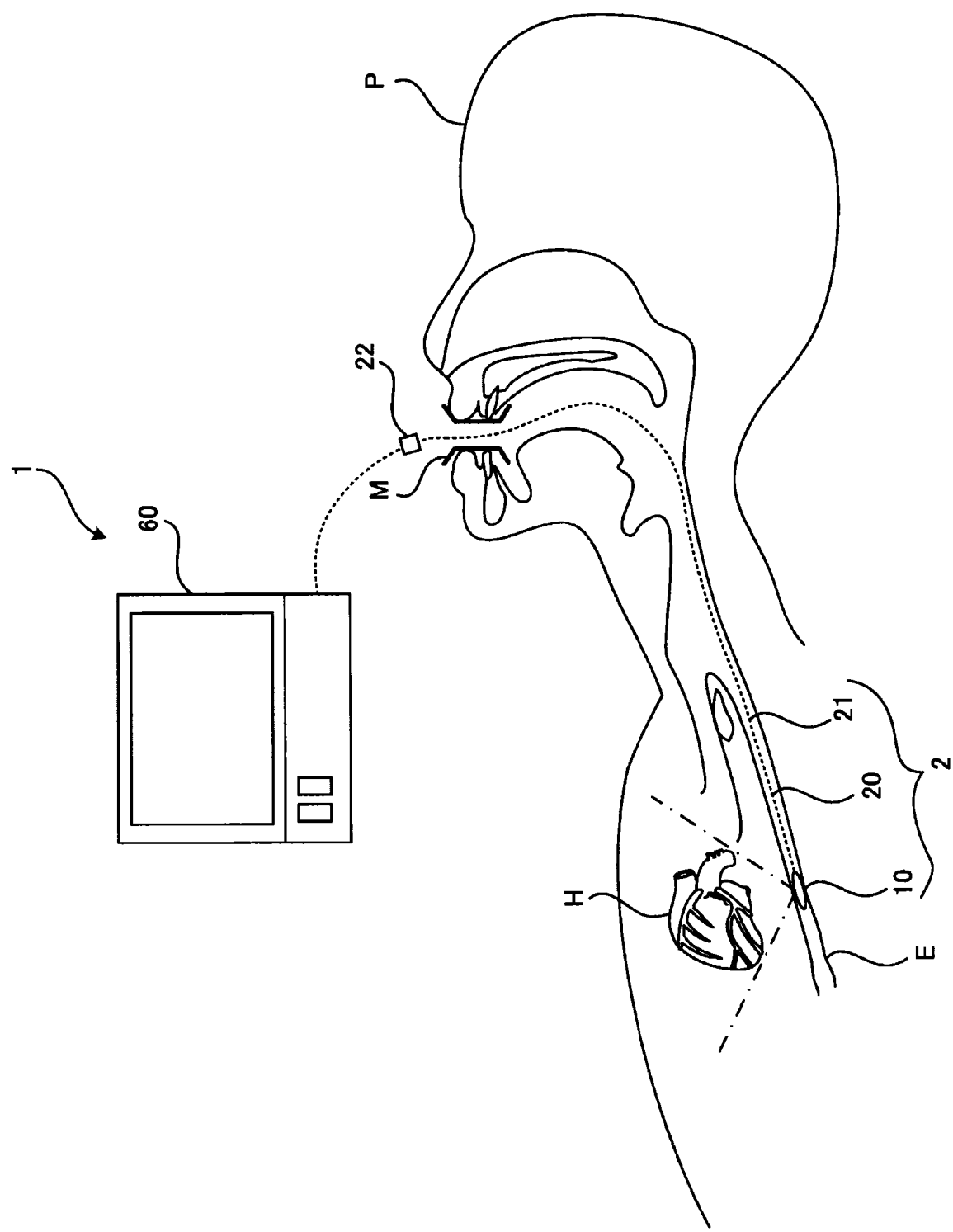
FIG. 1 is a schematic view of an ultrasound diagnostic imaging device according to a first embodiment.

FIG. 1 shows an example in which an ultrasound diagnostic imaging device 1 as the present embodiment comprises a capsule-type main body 10 and is used for observation of the heart H. In this case, the main body 10 is set and maintained in a desired position in the esophagus E for generation and transmission of ultrasound waves to a desired organ (e.g., the heart H) of the subject P and for reception of reflected waves from the heart H as echo signals. In the following description, the transmission of ultrasound waves and the reception as reflected waves may be together referred to as "ultrasonic transmission and reception".

While the capsule-type main body 10 transmits echo signals to an external device 60, the external device 60 processes the signals being received from the capsule-type main body 10 and creates and displays ultrasound images. Incidentally, the heart H shown in each drawing is schematically depicted as a simple reminder that the observed object in the present embodiment is the heart H.

In the following discussion, if the ultrasound diagnostic imaging device 1 is mentioned, then its configuration includes an ultrasound medical device 2 and an external device 60. In addition, if the ultrasound medical device 2 is mentioned, then its configuration includes a capsule-type main body 10 and a guiding hollow tube 20. These devices 1 and 2 are, however, designated as separate entities only for convenience of description, so the configuration is such that the ultrasound medical device 2 includes the ultrasound diagnostic imaging device 1.

Figure 2:
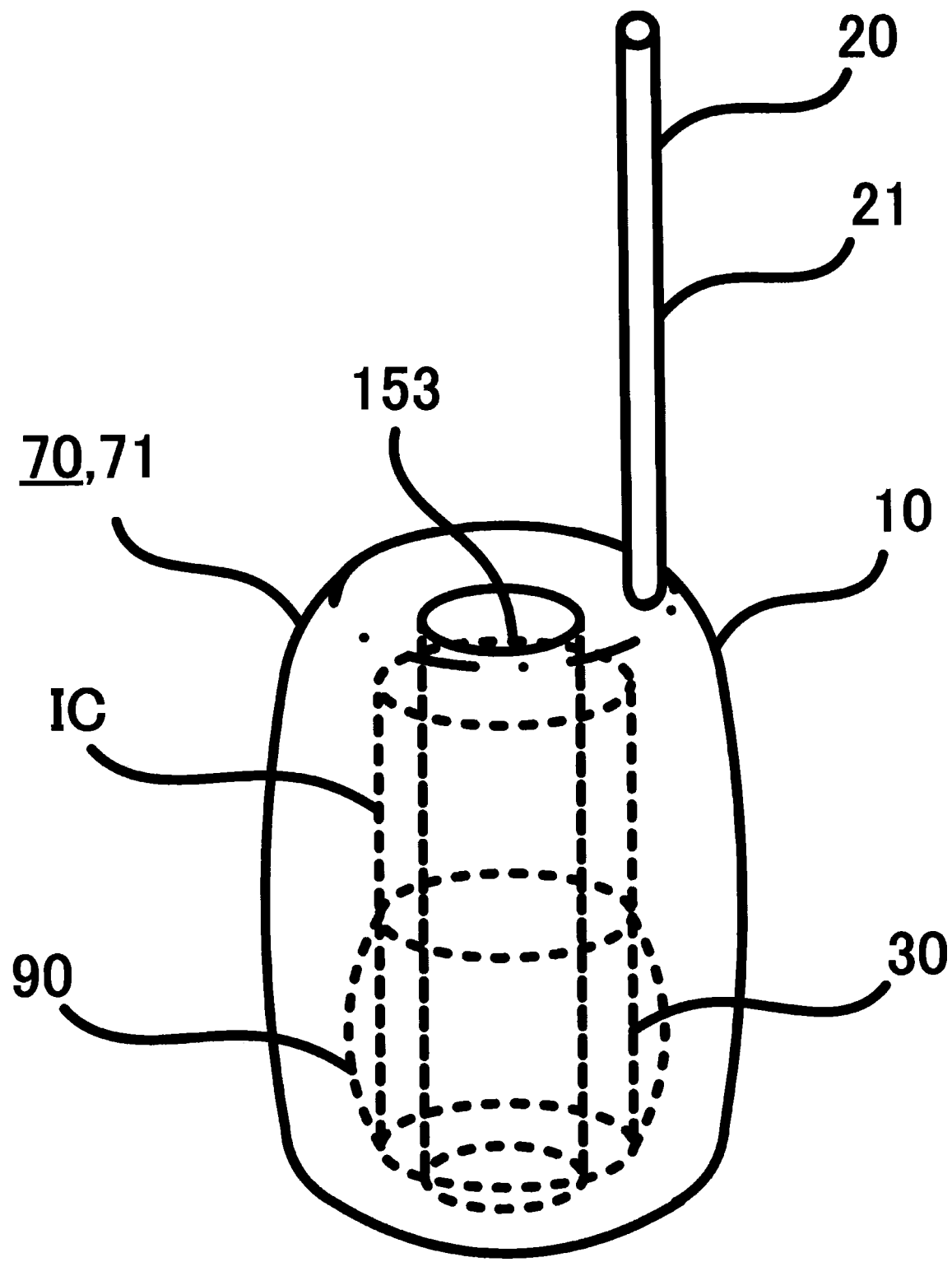
FIG. 2 is a perspective view of an ultrasound medical device.

FIG. 2 is a perspective view of the ultrasound medical device.

As shown in FIGS. 1 and 2, the ultrasound medical device comprises a capsule-type main body 10 and a guiding hollow tube 20. The guiding hollow tube 20 is depicted by a dashed line in FIG. 1, and the leading end part of the guiding hollow tube 20 is shown in FIG. 2. While the capsule-type main body 10 is attached on the leading end of the guiding hollow tube 20, the external device 60 is connected to the base end of the guiding hollow tube 20.

The capsule-type main body 10 and the guiding hollow tube 20 are both inserted into the esophagus E of the subject, and the capsule-type main body 10 is kept at a desired location in the esophagus E for use by being made to adhere to the wall of the esophagus E.

Figure 3:
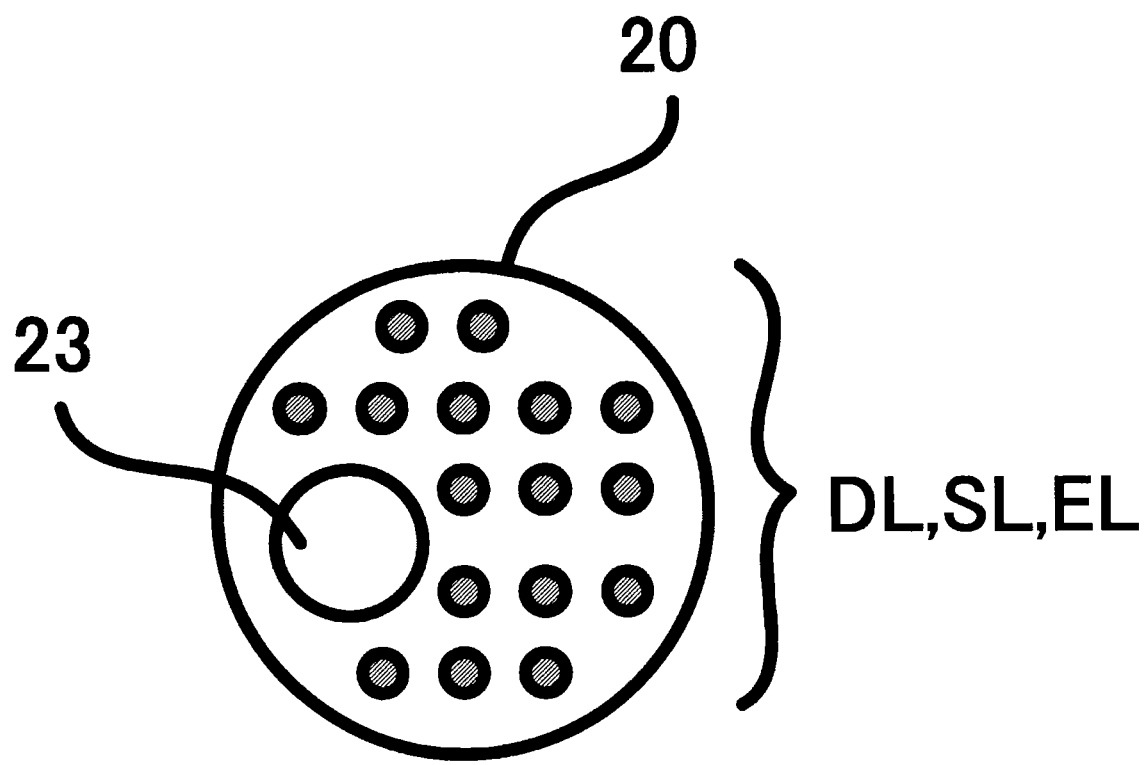
FIG. 3 is a cross-sectional view of a guiding hollow tube.

FIG. 3 is a cross-sectional view of the guiding hollow tube 20. As shown in FIG. 3, the guiding hollow tube 20 comprises a hollow tube 23, which is a tube for injection and discharge of liquid into an expansion and contraction body 70 (described later). The details of the expansion and contraction body 70 and so on are described later.

In addition, the guiding hollow tube 20 contains a signal line SL, a power line EL and a data line DL respectively in place. The signal line SL, power line EL and data line DL are also detailed later.

(Capsule-Type Main Body 10)

Figure 4:
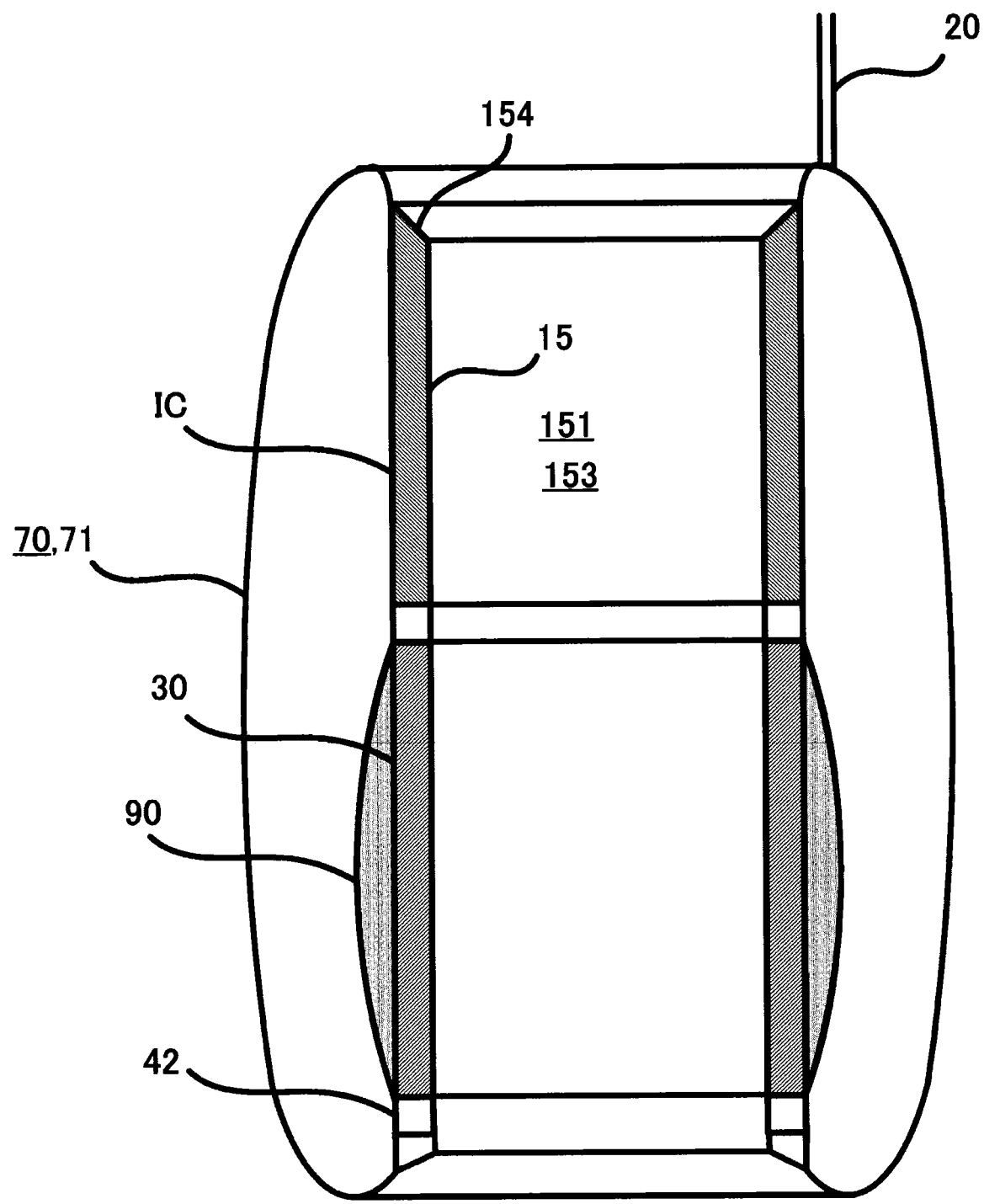
FIG. 4 is a longitudinally sectioned view showing the interior of a capsule-type main body.

FIG. 4 is a longitudinally sectioned view that shows the interior of the capsule-type main body 10. As shown in FIG. 4, the capsule-type main body 10 comprises a support 15, ultrasound transducers 30, the expansion and contraction body 70, and an acoustic lens 90.

(Guiding Hollow Tube 20)

As shown in FIGS. 1 and 2, the guiding hollow tube 20 comprises a string-like body 21.

Figure 13:
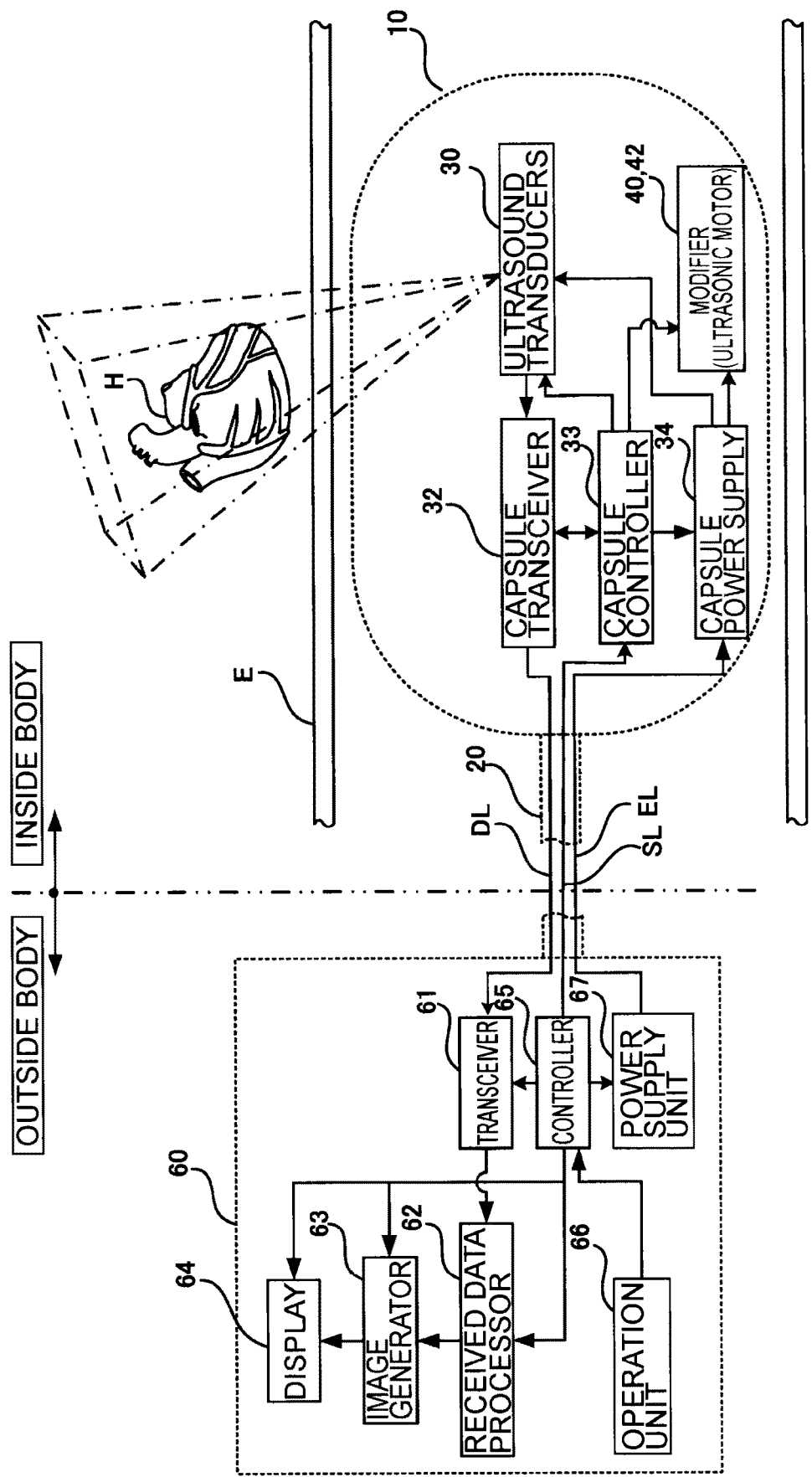
FIG. 13 is a block diagram showing the configuration of the ultrasound diagnostic imaging device.

Inside the string-like body 21, disposed respectively are the power line EL, signal line SL and data line DL (refer to FIG. 13). The power line EL is for sending electrical power from the external device 60 to the capsule-type main body 10. The signal line SL is for transmitting and receiving signals (control signals) between the external device 60 and the capsule-type main body 10. The data line DL is for transmitting waves reflected from the subject P (echo signals) that are received by the ultrasound transducers 30, from the capsule-type main body 10 to the external device 60.

A material for coating the power line EL and so on is selected from those usable in body cavities of living beings, and the selected material should have a softness that does not burden the subject P while it is left in the pharynx.

The string-like body 21 is provided with a marker 22 that indicates a particular distance (length) from the capsule-type main body 10. The marker 22 is implemented in a shape and a color that are visually recognizable. An example of the marker 22 may be graduating marks. As a specific example, in a case where the capsule-type main body 10 is disposed in the esophagus E for observation of the heart H, the marker 22 is provided on the string-like body 21, based on a general length from the oral cavity to an approximate spot (hereinafter referred to as the predetermined location) in the esophagus E where the heart H can be observed. The medical specialist, while pushing the string-like body 21 and inserting the capsule-type main body 10 into the esophagus E, checks the position of the marker 22. By doing so, when the marker 22 has come near to the oral vicinity, the medical specialist can easily recognize that the capsule-type main body 10 has arrived at the predetermined location in the esophagus E. Incidentally, for example, one end of the string-like body 21 can be fixed on a mouthpiece M that is disposed in the oral cavity of the subject P for preventing the inserted capsule-type main body 10 from moving farther by the peristalsis of the esophagus E.

(Ultrasound Transducers 30)

The ultrasound transducers 30 are installed in the capsule-type main body 10, and the ultrasound transducers 30 transmit ultrasound waves from their radiating surfaces, based on driving signals received from a capsule controller 33 (refer to FIG. 13). The ultrasound transducers 30 also receive waves reflected by the subject P (echo signals) and send them to a capsule transceiver 32 (refer to FIG. 13).

Each ultrasound transducer 30 comprises a matching layer, a piezoelectric transducer, and a backing material. In FIG. 4, the ultrasound transducers 30 are shown each as an integration of a matching layer, a piezoelectric transducer, and a backing material.

(Acoustic Lens 90)

The acoustic lens 90 is disposed on the surface of each ultrasound transducer 30 (i.e., on the side where ultrasound waves are emitted), and the acoustic lens 90 circumferentially constricts the ultrasonic beam around the cylindrical tube. The matching layer is disposed between each piezoelectric transducer and the tissue of a living body, so it has a predetermined acoustic impedance that is intermediate between them. The piezoelectric transducer converts electrical signals into ultrasonic signals, and it also converts ultrasonic signals into electrical signals in the opposite direction. The backing material is disposed on the back of the piezoelectric transducer and absorbs acoustic energy that is being radiated backward.

(Support 15)

Figure 5:
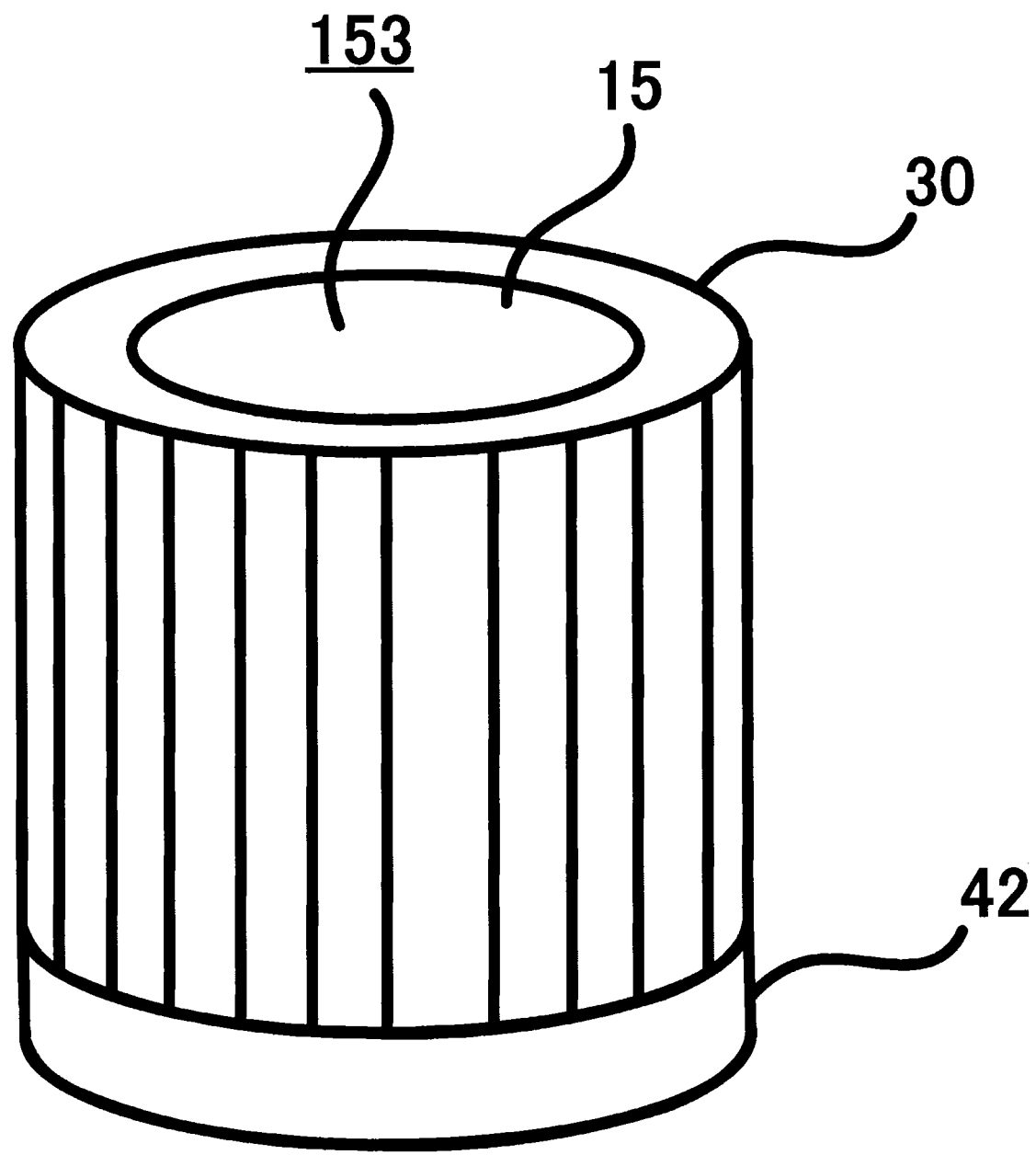
FIG. 5 is a perspective view of a plurality of ultrasound transducers arranged in one dimension along the circumference.
Figure 6:
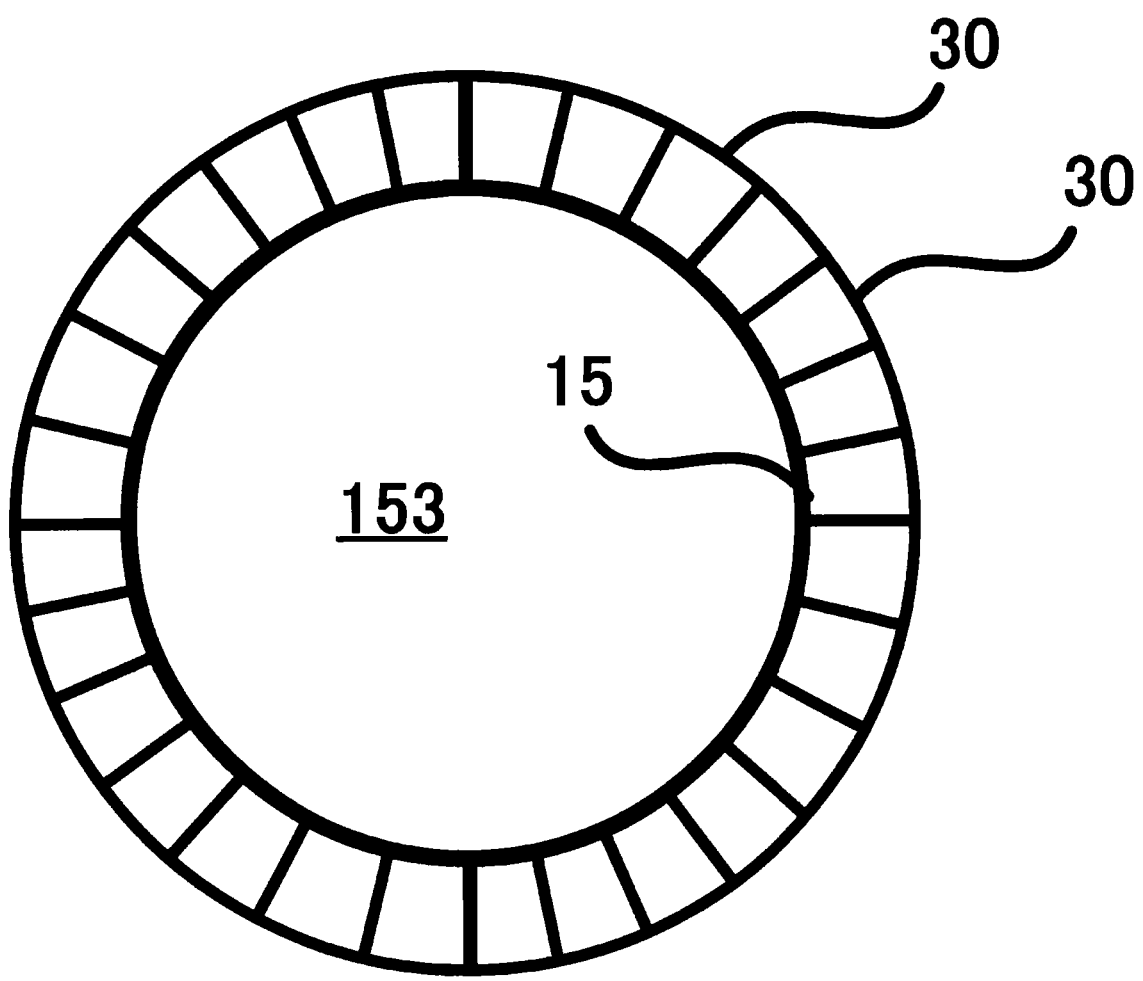
FIG. 6 is a plan view of the one-dimensionally arranged ultrasound transducers.

FIG. 5 is a perspective view showing a plurality of ultrasound transducers that are one-dimensionally arranged along the circumference; FIG. 6 is a plan view of the one-dimensionally arranged ultrasound transducers; and FIG. 7 is a front view of the one-dimensionally arranged ultrasound transducers shown sectionally in a plane that includes the axis of the cylindrical tube.

Figure 7:
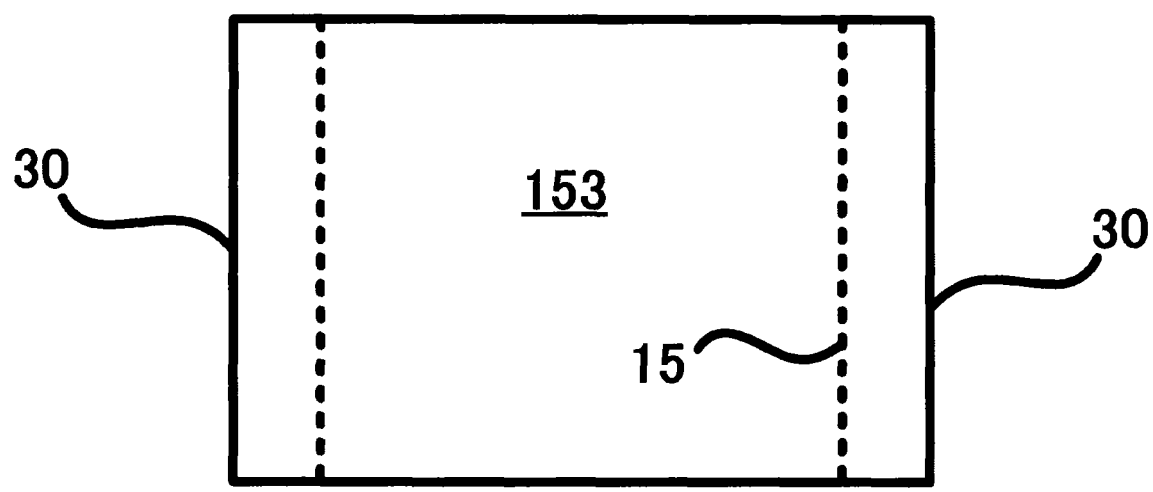
FIG. 7 is a front view of the one-dimensionally arranged ultrasound transducers.
Figure 23:
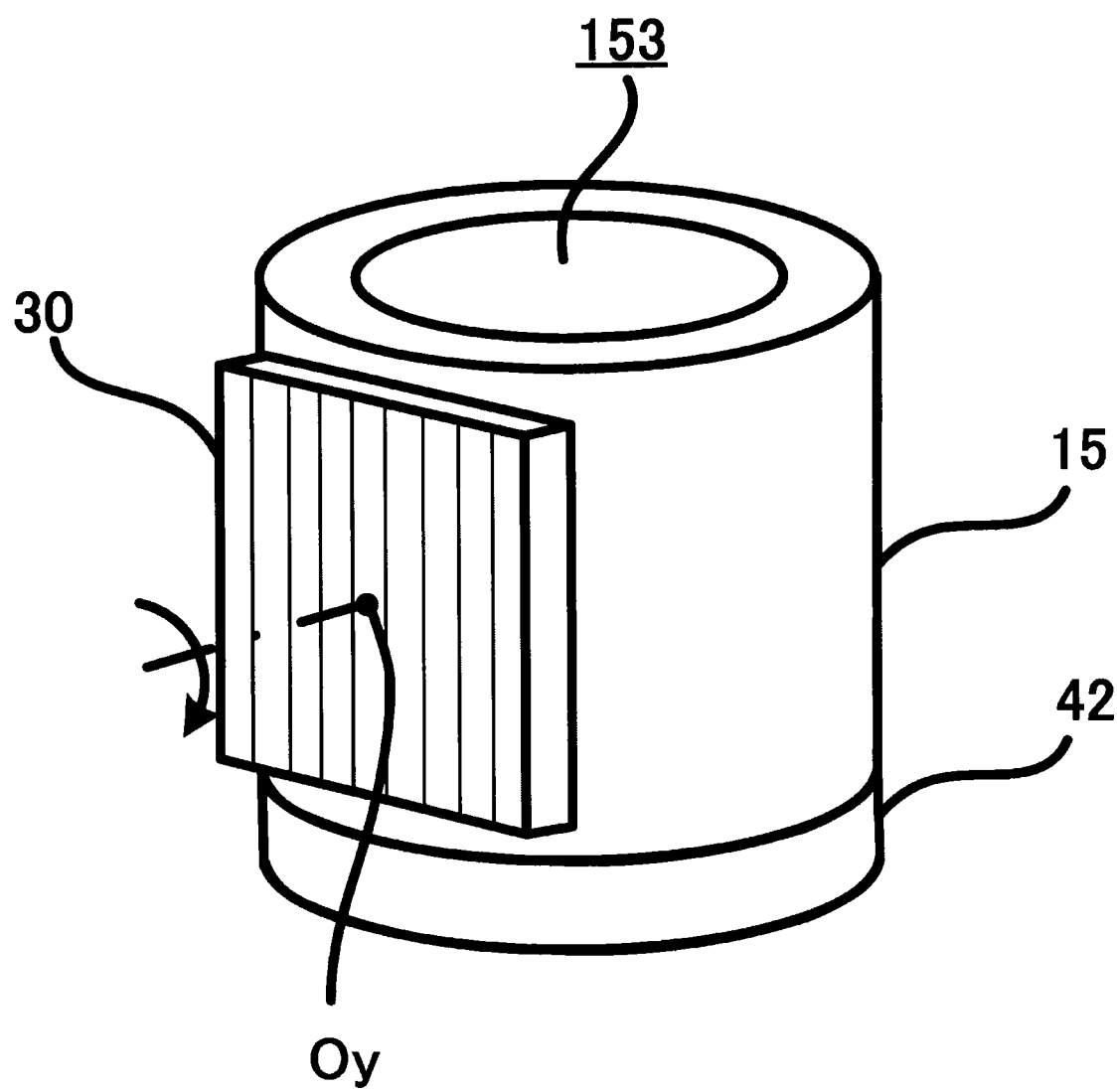
FIG. 23 is a perspective view of ultrasound transducers that have been arranged into a flat board and placed externally on a support, as a seventh embodiment.
Figure 24:
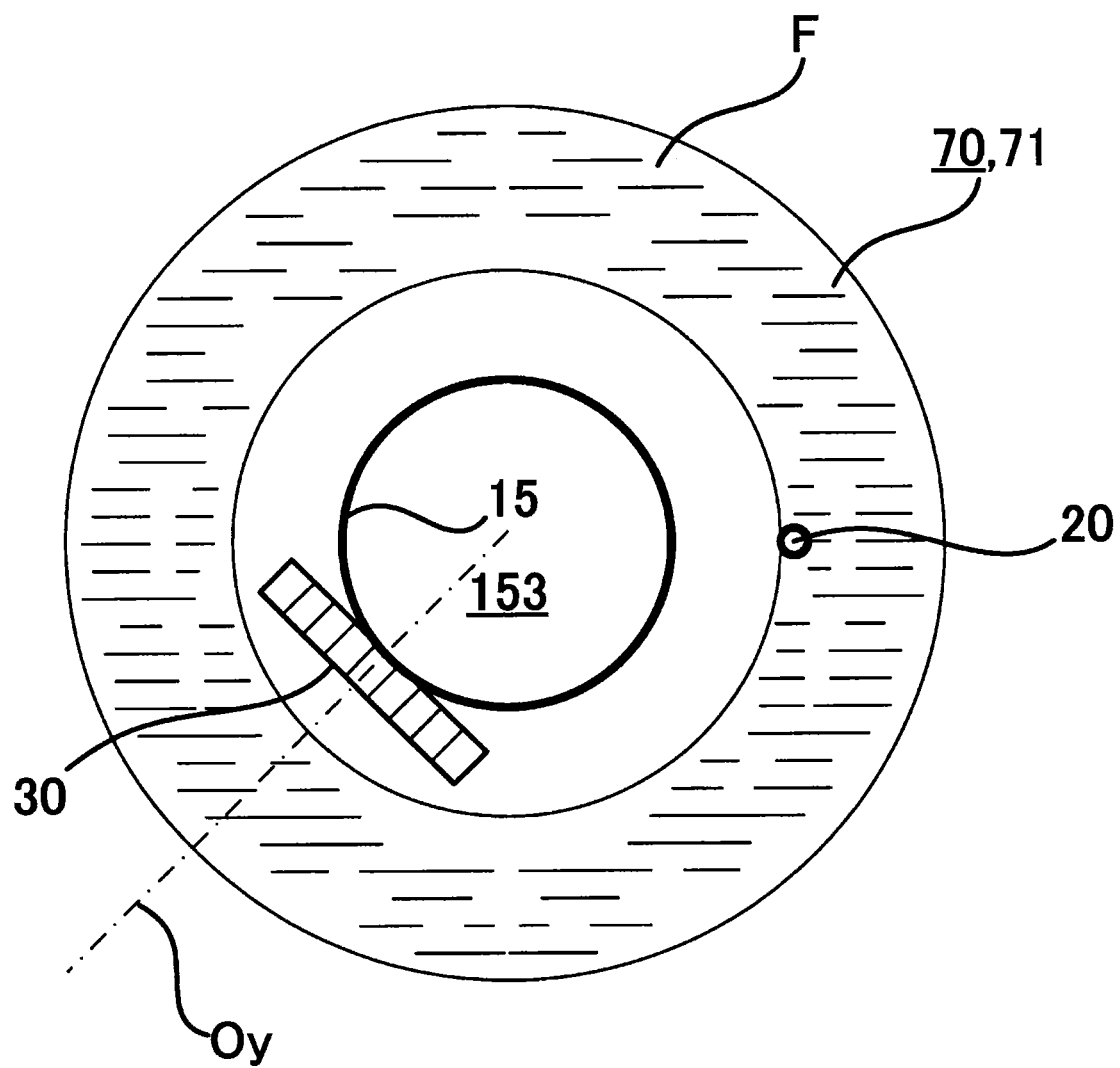
FIG. 24 is a cross-sectional view of the capsule-type main body with its expansion and contraction body inflated.

As shown in FIG. 5 through FIG. 7, the ultrasound transducers 30 are disposed in a cylindrical arrangement or in an approximately partially cylindrical arrangement (e.g., over a quarter around), or are arranged in a flat board form. Here, the ultrasound transducers 30 are arranged in a cylindrical tube as a radial array type, which is shown in FIG. 4 through FIG. 6. The ultrasound transducers 30 are disposed on the support 15, which has a cylindrical tube form. By the way, the piezoelectric transducers may be arranged on a backing material that has been formed in a cylindrical tube. In such a case, the support 15 itself is made of a backing material. Incidentally, the tube axis of the cylindrical tube may be simply referred to as "the rotation axis", "the rotation axis of the ultrasound transducers", or "the rotation axis of the support". Furthermore, the ultrasound transducers 30 arranged in a flat board form are shown in FIG. 23 and FIG. 24.

The support 15 is mounted with an integrated circuit IC that includes control means (a capsule controller 33, which is described later) for controlling the ultrasound transducers 30. The integrated circuit IC is tubular in the same way as the ultrasound transducers 30 and is placed coaxially in a tubular form above the ultrasound transducers 30. In the tubular integrated circuit IC, the axial length of the tube of the integrated circuit IC is about 10 mm. At the tubular entry opening of the integrated circuit IC (the opening at the top in FIG. 4 and FIG. 8), provided is a slanted face 154, which is smoothly continuous to a through-hole 153 (described later). With the provision of the slanted face 154, fluid food and catheters (described later) are made to easily pass through the through-hole 153, directly or indirectly. Incidentally, the support 15 may be provided also with a surface that functions the same way as the slanted face 154.

The ultrasound transducers 30, which are arranged in a tubular form, have an axial length of about 10 mm in the tubular arrangement of the ultrasound transducers 30. Incidentally, the axial length of the acoustic lens 90 is also about 10 mm. By the way, the axial length of the support 15 is approximately 24 mm. At the upper end and the lower end of the support 15, fixing spaces of from 1.0 to 3.0 mm are provided, respectively, for fixing an expansion and contraction body 70 (which is described later).

The support 15 has a through-hole 153 passing axially through the tube, so that the function of the esophagus E is maintained even after the capsule-type main body 10 has been inserted in the esophagus E. Incidentally, in a case where piezoelectric transducers or the like are arranged on a tube-form backing material, the through-hole 153 is configured by the backing material.

The through-hole 153 is a hole that lets through fluid food and water. Fluid food and water may be directly let through the through-hole 153 or may be indirectly let through the through-hole 153 by means of a catheter. In the latter case, the through-hole 153 has a diameter larger than that of the catheter by approximately 2.0 mm.

Furthermore, the through-hole 153 may be a hole that can let through a transnasal endoscope (not shown). For example, if the transnasal endoscope has a diameter of 6.0 mm, then the through-hole 153 has a diameter of, for example, 8.0 mm, which is larger than the diameter of the transnasal endoscope by approximately 2.0 mm.

(Expansion and Contraction Body 70)

Figure 8:
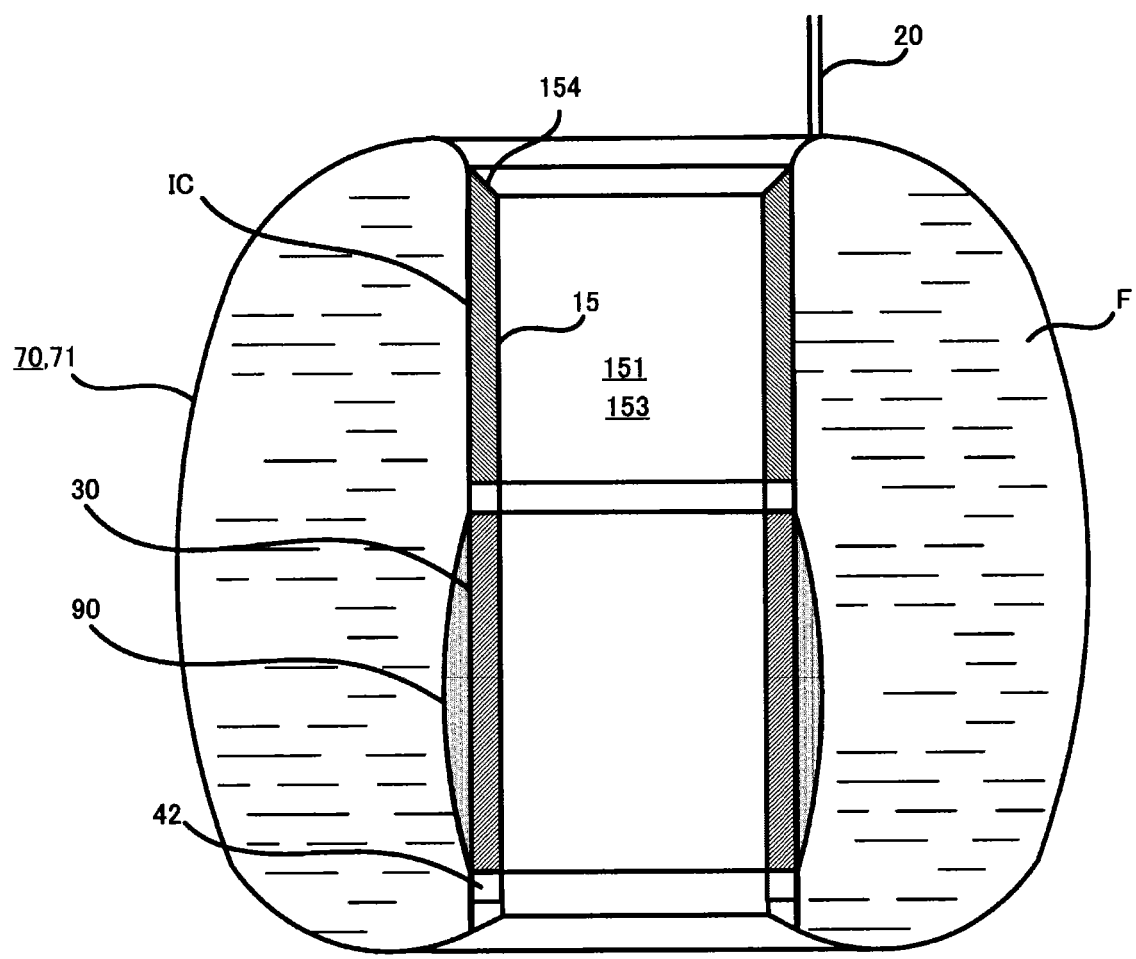
FIG. 8 is a longitudinally sectioned view of the capsule-type main body with its expansion and contraction body inflated.
Figure 9:
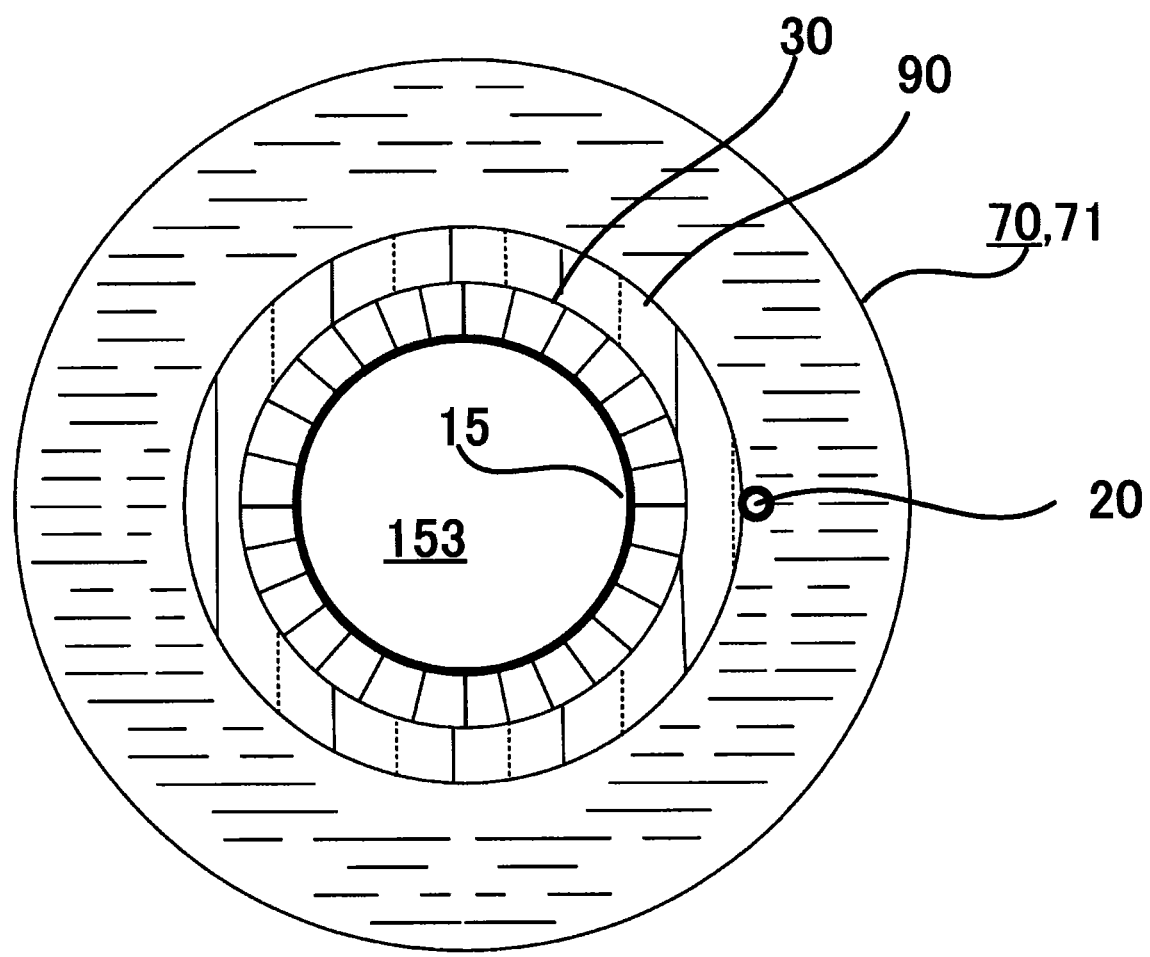
FIG. 9 is a cross-sectional view of the same shown in FIG. 8.

Now, the expansion and contraction body 70 is described with reference to FIG. 4, FIG. 8 and FIG. 9. FIG. 8 is a longitudinally sectioned view of the capsule-type main body with its expansion and contraction body inflated, and FIG. 9 is a cross-sectional view of the body shown in FIG. 8.

As shown in FIG. 4, the expansion and contraction body 70 is disposed circumferentially to shield a plurality of ultrasound transducers, which are arranged in a tubular form. FIG. 4 and FIG. 8 show the expansion and contraction body 70, which is disposed to shield the acoustic lens 90 circumferentially.

The expansion and contraction body 70 has a bag-like container 71 that is configured expandable to come into contact with the wall of the esophagus E when a filling liquid is sent through a hollow tube 23 from outside the body, and it is shrinkable by draining the liquid. FIG. 4 shows the bag-like container 71 in its shrunken state while FIG. 8 and FIG. 9 show the bag-like container 71 in its expanded state. Incidentally, for example, the external device 60 may be provided with a liquid supply (refer to FIG. 13), and from there, the liquid is led to fill the bag-like container 71.

The bag-like container 71 is molded of a material that has elasticity and is safely usable in body cavities, and the bag-like container 71 is connected to the hollow tube 23. The liquid used for filling the bag-like container 71 is an ultrasound-transmissive medium that has an acoustic impedance approximately equal to the human body, for example, sterile water. FIG. 8 shows the liquid "F" filling there.

When the capsule-type main body 10 is inserted into the esophagus E, the bag-like container 71 is kept shrunken (refer to FIG. 4). The external diameter of the capsule-type main body 10 with the bag-like container 71 shrunken is approximately 14 mm. Shrinking the bag-like container 71 enables easy insertion of the capsule-type main body 10 into the esophagus E, resulting in little burden to the subject P.

After the capsule-type main body 10 has been inserted at a predetermined location in the esophagus E, the bag-like container 71 is inflated (refer to FIG. 8). The external diameter of the capsule-type main body 10 with the bag-like container 71 inflated is approximately 30 to 40 mm. With the inflated bag-like container 71 adhering to the wall of the esophagus E, the capsule-type main body 10 is kept in place at the predetermined location in the esophagus E. In this state, the internal body of the subject P is observable. With the bag-like container 71 being made to adhere to the wall of the esophagus E, the capsule-type main body 10 is kept in place in the esophagus E. In this state, fluid food, etc. can be fed through the through-hole 153, directly or indirectly. It is, therefore, possible that the capsule-type main body 10 is kept there for a long period of time.

The bag-like container 71 is deflated before the capsule-type main body 10 is pulled out of the esophagus E. This allows easy pulling out of the capsule-type main body 10 from the esophagus E, with reduced burden to the subject P.

At the inlet of the expansion and contraction body 70 (the opening at the top end in FIG. 4 and FIG. 8), provided is a guiding face 72 (refer to FIG. 15), which is smoothly continuous to the slanted face 154. This configuration enables easy passage of fluid food, etc. through the through-hole 153, directly or indirectly.

(Modifier 40)

Now, the modifier 40, which modifies the angle of the beam of ultrasound waves emitted from the ultrasound transducers 30, is described with reference to FIGS. 4, 5 and 10.

The modifier 40 is integrated in the capsule-type main body 10. In the following description, the modifier 40 is described to modify circumferentially the angle of the ultrasound transducers 30 and to retain the modified angle.

Figure 10:
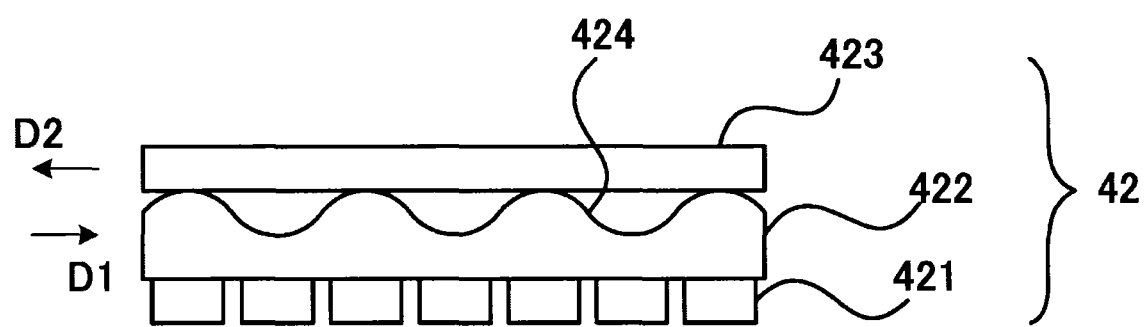
FIG. 10 is a schematic view of an ultrasonic motor.

FIG. 10 is a schematic view of an ultrasonic motor 42. As shown in FIG. 10, the ultrasonic motor 42 comprises piezoelectric ceramics 421, a stator 422, and a rotor 423. They are disposed at one end of the support 15 (at the lower end in FIGS. 4 and 5). For example, the piezoelectric ceramics 421 and the stator 422 are provided on the support 15 while the rotor 423 is provided on the ultrasound transducers 30. The stator 422 and the rotor 423 have each a circular form along the circumference of the ultrasound transducers 30.

The piezoelectric ceramics 421 are disposed opposite to the rotor 423, with the stator 422 positioned therebetween, and the piezoelectric ceramics 421 are pasted on the stator 422. The surface 424 of the side where the stator 422 is not pasted has a wave-like shape and is in contact with the rotor 423. Incidentally, the rotor 423 may be provided on the support 15 while the piezoelectric ceramics 421 and the stator 422 may be provided on the ultrasound transducers 30.

The piezoelectric ceramics 421 are driven to make an oscillation (expansion and contraction) by the application of a high-frequency voltage to the piezoelectric ceramics 421. As a result, traveling waves are generated on the surface of the stator 422, and the rotor 423 is made to move in the direction opposite to that of the traveling waves. However, since the rotor 423 is fixed, the ultrasound transducers 30 will make a turning movement around the axis of rotation 31 (circumferential direction) relative to the support 15.

The capsule-type main body 10 is provided with a capsule controller 33 (refer to FIG. 13) for controlling the ultrasonic motor 42 and a capsule power supply 34 (refer to FIG. 13) for supplying electrical power to the ultrasonic motor 42.

The capsule controller 33 outputs, to the modifier 40, instructions "to make a modification in the rotational angle" and "to terminate the modification", which instructions have been received from the controller 65. The modifier 40, upon receiving an instruction "to make a modification in the rotational angle", generates a high-frequency voltage and sends it to the piezoelectric ceramics, and thus makes the piezoelectric ceramics oscillate (expand and contract). In this way, a modification is being made to the rotation angle of the ultrasound transducers 30.

Then, the modifier 40, upon receiving an instruction "to terminate the modification", stops feeding the high-frequency voltage to the piezoelectric ceramics 421. As a result, the piezoelectric ceramics 421 are made to stop oscillating and to retain the rotation angle of the ultrasound transducers 30.

(Positioning of the Capsule-Type Main Body and Pulling it Back)

Now, the positioning of the capsule-type main body and pulling it back are explained.

The capsule-type main body 10 moves in the esophagus E by the peristalsis of the esophagus E or by body movements.

While the capsule-type main body 10 is being positioned in the esophagus E, for example, if it has progressed too far by the peristalsis, then "pulling back" is necessary, in which the capsule-type main body 10 is made to retrogress by operating the guiding hollow tube 20.

Likewise, while the capsule-type main body 10 is positioned at a predetermined location in the esophagus E for a long-term observation, "pulling it back" is necessary with the guiding hollow tube 20. Incidentally, if one end of the string-like body 21 is fixed on the mouthpiece M, which has been disposed in the oral cavity of the subject P, for preventing the capsule-type main body 10 from progressing by the peristalsis of the esophagus E, then, "pulling it back" may not be necessary. When the observation is terminated, however, the capsule-type main body 10 should be removed out of the body by the "pulling it back".

(Production of the Capsule-Type Main Body 10)

Figure 11:
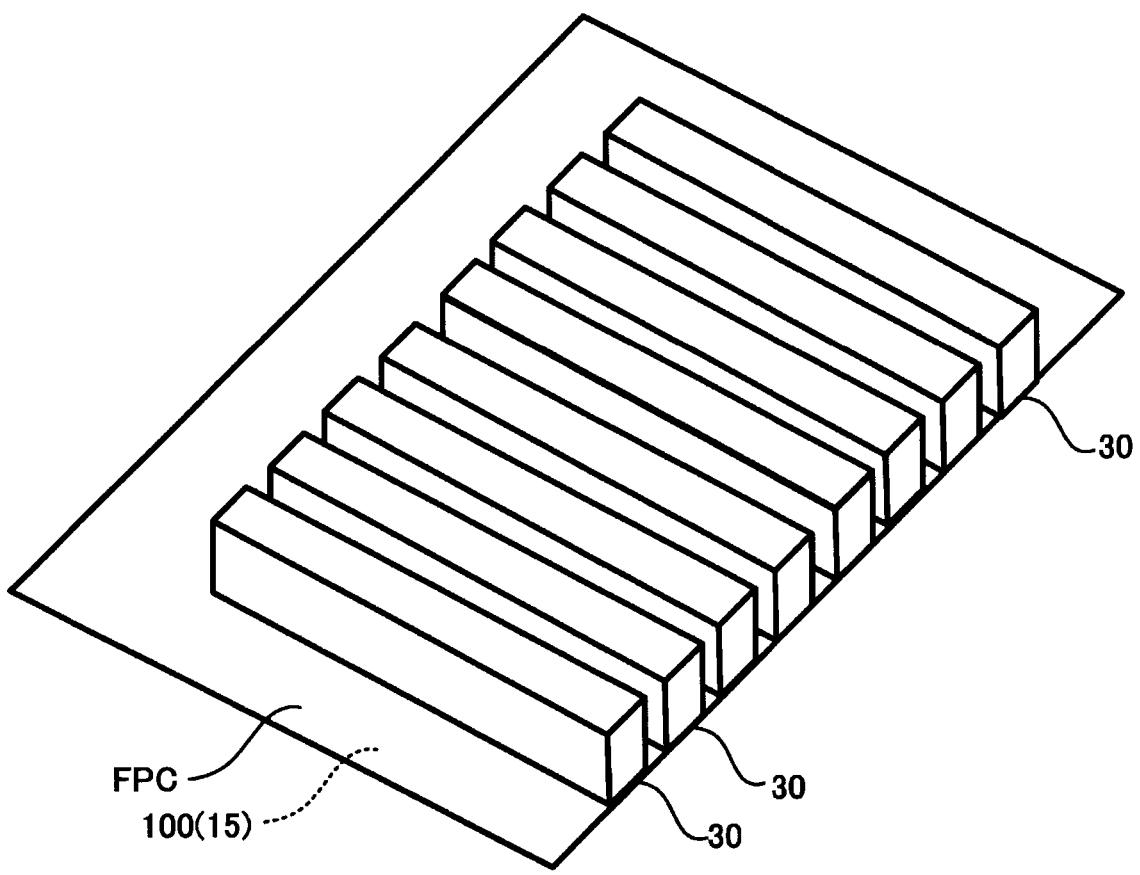
FIG. 11 is a perspective view of a plurality of ultrasound transducers arranged on a flexible printed circuit board.

Now, an example of manufacturing process of the capsule-type main body 10 is explained with reference to FIG. 11, which is a perspective view of a plurality of ultrasound transducers that are aligned on a flexible printed circuit board.

At first, strip-like ultrasound transducers 30 are fixed on a flexible printed circuit (FPC) (as a subassembly).

Then, this is patched on a shape-memory alloy plate 100 to construct a tubular probe. In this case, the shape-memory alloy plate 100 works as the support 15, and the shape-memory alloy plate 100 has such a property as to assume a flat tabular form at a predetermined temperature (at the body temperature, or, e.g., at a temperature lower than 20 degrees C.) and a circular tubular form when heated to a higher temperature.

For example, at a temperature lower than 20 degrees C., the shape-memory alloy plate 100 is joined to the subassembly, and then heated, for example, to 25 degrees. This causes the combined body to assume a circular tubular form that functions as the support 15 with a plurality of ultrasound transducers 30 aligned along the circumference of the support 15. Incidentally, all electrodes are extended from the FPC. By mounting an integrated circuit IC and other electronic components on the FPC, it is possible to execute all electrical circuit connections integrally on the FPC.

Then, the tubular support 15 is fitted in with a similarly tubular integrated circuit IC. Here, the integrated circuit IC is disposed above the ultrasound transducers 30, and the hollow part 151 of the support 15 is the through-hole 153. Incidentally, the above description is only an example of using a shape-memory alloy as the metal plate 100. Any general alloy without shape-memory property may be used as the metal plate 100.

Then, the acoustic lens 90 is attached to the surfaces (the sides from which ultrasound waves will be emitted) of the ultrasound transducers 30.

Then, the expansion and contraction body 70 is fixed to the upper and lower ends of the support 15.

Then, the hollow tube 23 is connected to the expansion and contraction body 70. Before or after this step, the data line DL, the signal line SL and the power line EL are connected, respectively, to the capsule transceiver 32, to the capsule controller 33, and to the capsule power supply 34 (refer to FIG. 13).

(Actions of the Ultrasound Medical Device)

The above description has been about the configuration of the ultrasound medical device.

Figure 12:
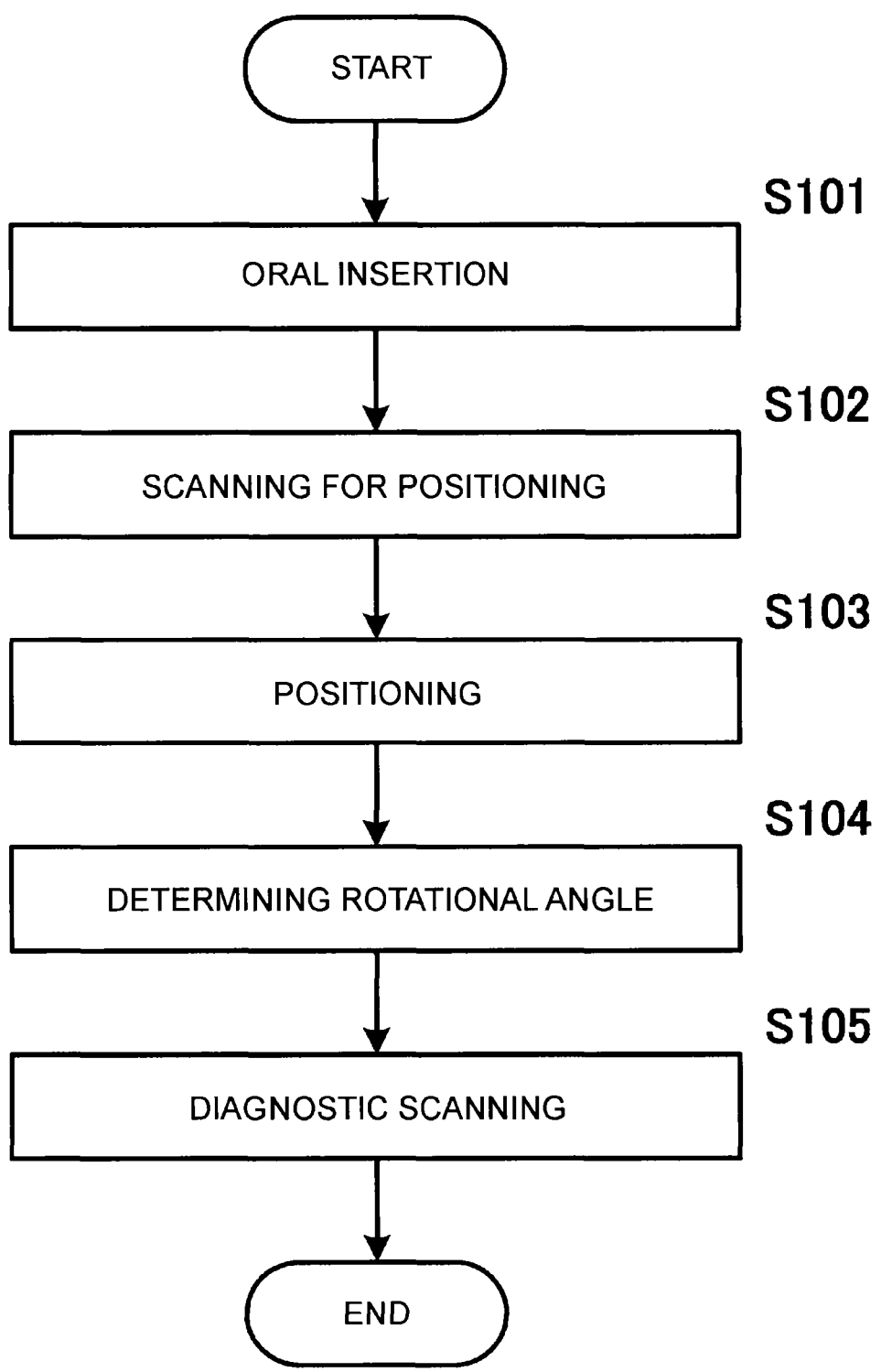
FIG. 12 is a flowchart showing a series of actions being taken for observing the internals of the subject by using the ultrasound medical device.

Now, actions taken by the ultrasound medical device are described with reference to FIG. 12, which is a flowchart showing a series of actions taken when the internals of the subject are to be observed by using the ultrasound medical device.

At first, the ultrasound transducers 30 are inserted orally into the esophagus E (S101).

When the ultrasound transducers 30 have been inserted to a certain extent, scanning is started for positioning (S102). By doing so, the user can readily insert and position the capsule-type main body 10 at a predetermined location in the esophagus E by watching it in image. At the same time, the string-like body 21 is also inserted into the esophagus E.

Then, the positioning of the ultrasound transducers 30 is performed (S103). The positioning of the ultrasound transducers 30 is executed, as mentioned above, by performing steps of making the bag-like container 71 "adhere" to the esophagus E by inflating it, and of "pulling it back" with the guiding hollow tube 20. In the positioning, the capsule-type main body 10 is first let proceed beyond a planned laid-in location and then "pulled back" while being monitored in image. By pulling the string-like body 21, the capsule-type main body 10 is made to recede to the planned laid-in location.

Then, the rotational angle of the ultrasound transducers 30 is modified with the modifier 40, while being monitored in image (S104). Here, for example, the image should include an image of the heart, which is the observation object in this case.

In the above explained way, the ultrasound transducers 30 are positioned, their rotational angle is modified, and the capsule-type main body 10 is fixed at a predetermined location in the esophagus E before the starting of diagnostic scanning (S105).

While the capsule-type main body 10 is kept in place in the esophagus E, fluid food, a transnasal endoscope, or the like can be passed through the through-hole 153, directly or indirectly. Consequently, the function of the esophagus E is maintained.

(Basic Configuration of the Ultrasound Diagnostic Imaging Device)

Now, the basic configuration of the ultrasound medical imaging device is briefly described with reference to FIG. 13, which is a block diagram showing the configuration of the ultrasound diagnostic imaging device.

(Other Inside Constituents of the Capsule-Type Main Body)

Now, a description is given of the configuration inside the capsule-type main body 10.

The capsule-type main body 10 includes, as mentioned above, the ultrasound transducers 30 and the modifier 40.

In addition to these, the capsule-type main body 10 includes a capsule transceiver 32, a capsule controller 33, and a capsule power supply 34.

The capsule transceiver 32 sends control signals received from the external device 60 (controller 65, described later) to the capsule controller 33, and the capsule controller 33 sends driving signals to the ultrasound transducers 30, based on the control signals. The capsule transceiver 32 then receives echo signals that the ultrasound transducers 30 have received. In this embodiment, the sending and receiving of control signals between the capsule-type main body 10 and the external device 60 is executed through the signal line SL, which is disposed inside the string-like body 21.

As a specific example, the capsule controller 33 supplies driving signals to the ultrasound transducers 30 for execution of scanning, and ultrasound waves are emitted to the heart H. The capsule controller 33 comprises, for example, a clock generator, a transmission-delay circuit, and a pulsar circuit (not shown). The clock generator generates clock signals that are used for setting transmission frequencies and timings of emitting ultrasound waves. The transmission-delay circuit executes transmission-focusing by forcing delays to the transmission of ultrasound waves in accordance with the delays for convergence that make the ultrasound waves converge at a predetermined depth and the delays for inclination that make the ultrasound waves radiate in a predetermined direction. The pulsar circuit comprises pulsars in the same number as the individual channels assigned for the piezoelectric transducers. The pulsar circuit generates drive pulses (driving signals) at transmission timings having the delays and supplies the drive pulses (driving signals) to the piezoelectric transducers, which constitute the ultrasound transducers 30.

In addition, the capsule transceiver 32 executes delaying process on the echo signals received, and thereby, converts the analog echo signals to digital data, which are phased and added. The capsule transceiver 32 comprises, for example, a gain circuit, an A/D converter, a reception-delay circuit, and an adder (not shown). The gain circuit amplifies the echo signals that have been output from the piezoelectric transducers of the ultrasound transducers 30, for every reception channel (gain-processing). The A/D converter converts the amplified echo signals into digital signals. The reception-delay circuit provides delays that are necessary to set reception directionality on the echo signals that have been converted into digital signals. Specifically, the reception-delay circuit provides the digitized echo signals with the delays for convergence that make ultrasound waves from a predetermined depth converge, and with the delays for inclination that set reception directionality in a predetermined direction. The adder adds the echo signals that have been given the delays. By the addition, enhancement is made on the component of the reflection coming in the direction along the reception directionality. In other words, the reception-delay circuit and the adder function to phase and add the echo signals that have been obtained in a predetermined direction. The capsule transceiver 32 outputs the echo signals that have gone through the delaying process, to the external device 60.

The capsule transceiver 32 modulates the echo signals with carrier waves (carrier signals) at a predetermined frequency and outputs as electromagnetic waves from an antenna (not shown) to the external device 60 (transceiver 61 described later). The transmission and reception of the echo signals between the capsule-type main body 10 and the external device 60 is carried out through the data line DL, which is disposed in the string-like body 21.

The capsule power supply 34 receives electric power from the external device 60 and distributes the supplied electric power to the ultrasound transducers 30, to the capsule transceiver 32, and to the capsule controller 33. In this embodiment, the electric power is supplied from the external device 60 through the power line EL, which is disposed in the string-like body 21.

(External Device 60)

Now, the configuration of the external device 60 is described with reference to FIG. 13.

As shown in FIG. 13, the external device 60 is configured to include a transceiver 61, a received data processor 62, an image generator 63, a display 64, a controller 65, an operation unit 66, and a power supply unit 67.

The transceiver 61 receives the echo signals from the capsule transceiver 32 and outputs them to the received data processor 62.

The received data processor 62 executes various types of signal processing on the echo signals, which have been received from the transceiver 61. For example, the received data processor 62 comprises a B-mode processor. The B-mode processor receives the echo signals from the transceiver 61 and visualizes the amplitude information of the echo signals. In addition, the received data processor 62 may include a CFM (Color Flow Mapping) processor, which visualizes blood-flow information. The received data processor 62 may also include a Doppler processor. The Doppler processor here executes phase-detection on the echo signals, and thereby, extracts Doppler shift frequencies. The Doppler processor then executes FFT processing to show Doppler frequency distribution, which describes blood-flow velocity. The received data processor 62 outputs the echo signals that have been signal-processed, to the image generator 63.

The image generator 63 processes signals based on the reflected waves received with the ultrasound transducers 30 (the echo signals that have been through the signal processing and have been output from the received data processor 62) and creates image data (ultrasound image data).

The controller 65 controls the actions of all parts of the ultrasound diagnostic imaging device 1. For example, the controller 65 controls the actions of all parts of the ultrasound diagnostic imaging device 1 and the capsule-type main body 10. For example, the controller 65 generates transmission-timing signals for sending driving signals to drive the ultrasound transducers 30, for the capsule transceiver 32 through the capsule controller 33. It is also possible that the controller 65 causes the display 64 to display an image (ultrasound image) based on image data (ultrasound image data) that have been generated by the image generator 63. Incidentally, the configuration may be arranged such that the controller 65 sends transmission-timing signals to the capsule transceiver 32 through the transceiver 61. In this case, the signal line SL is not necessary.

The display 64 comprises a monitor like a CRT or a liquid crystal display. The operation unit 66 comprises such input devices as a keyboard and a mouse. The medical specialist instructs, through the operation unit 66, transmission, reception, etc. of ultrasound waves with the capsule-type main body 10.

Second Embodiment

Figure 14:
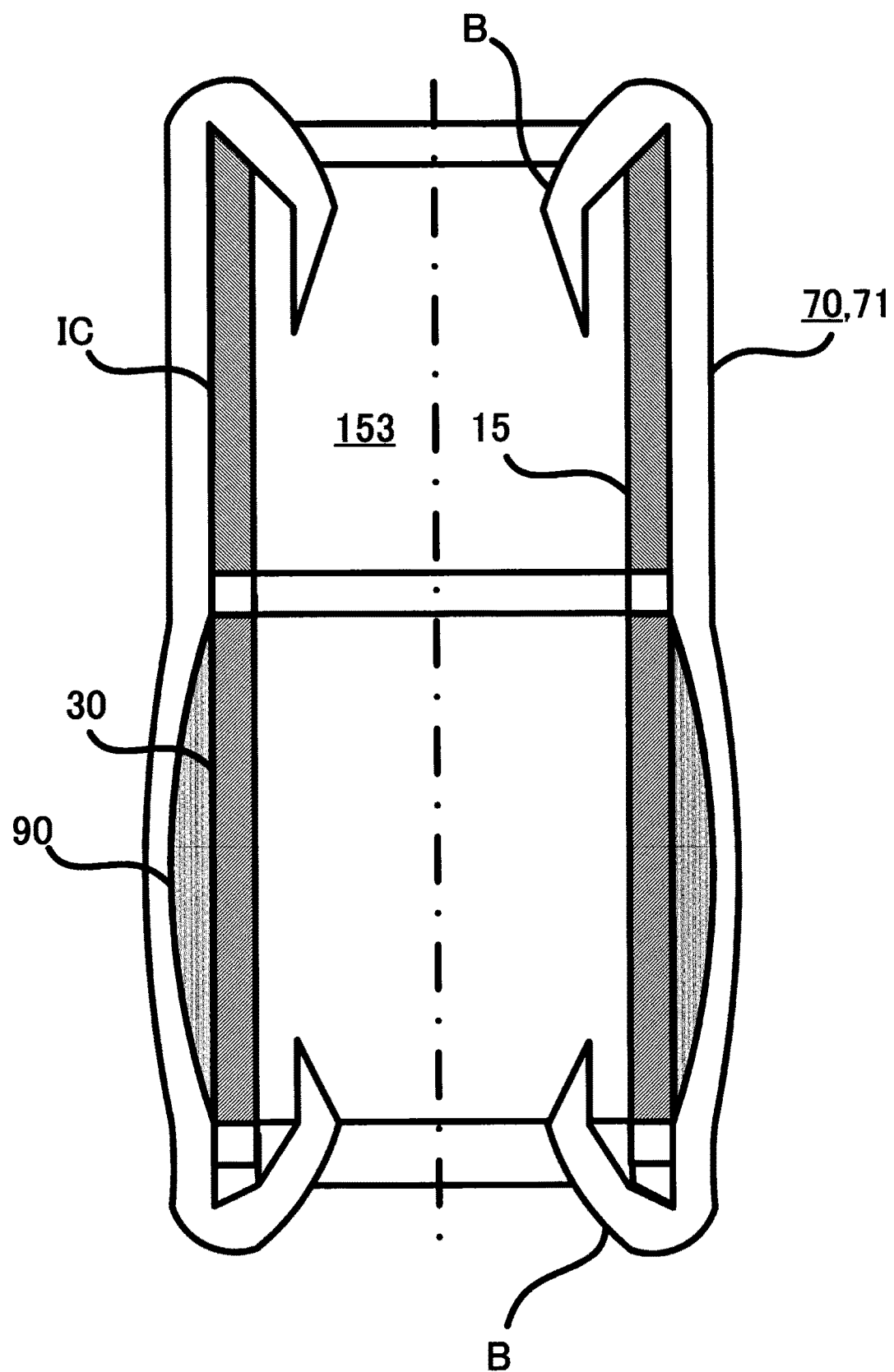
FIG. 14 is a longitudinally sectioned view of a capsule-type main body as a second embodiment, shown with its expansion and contraction body inflated.
Figure 15:
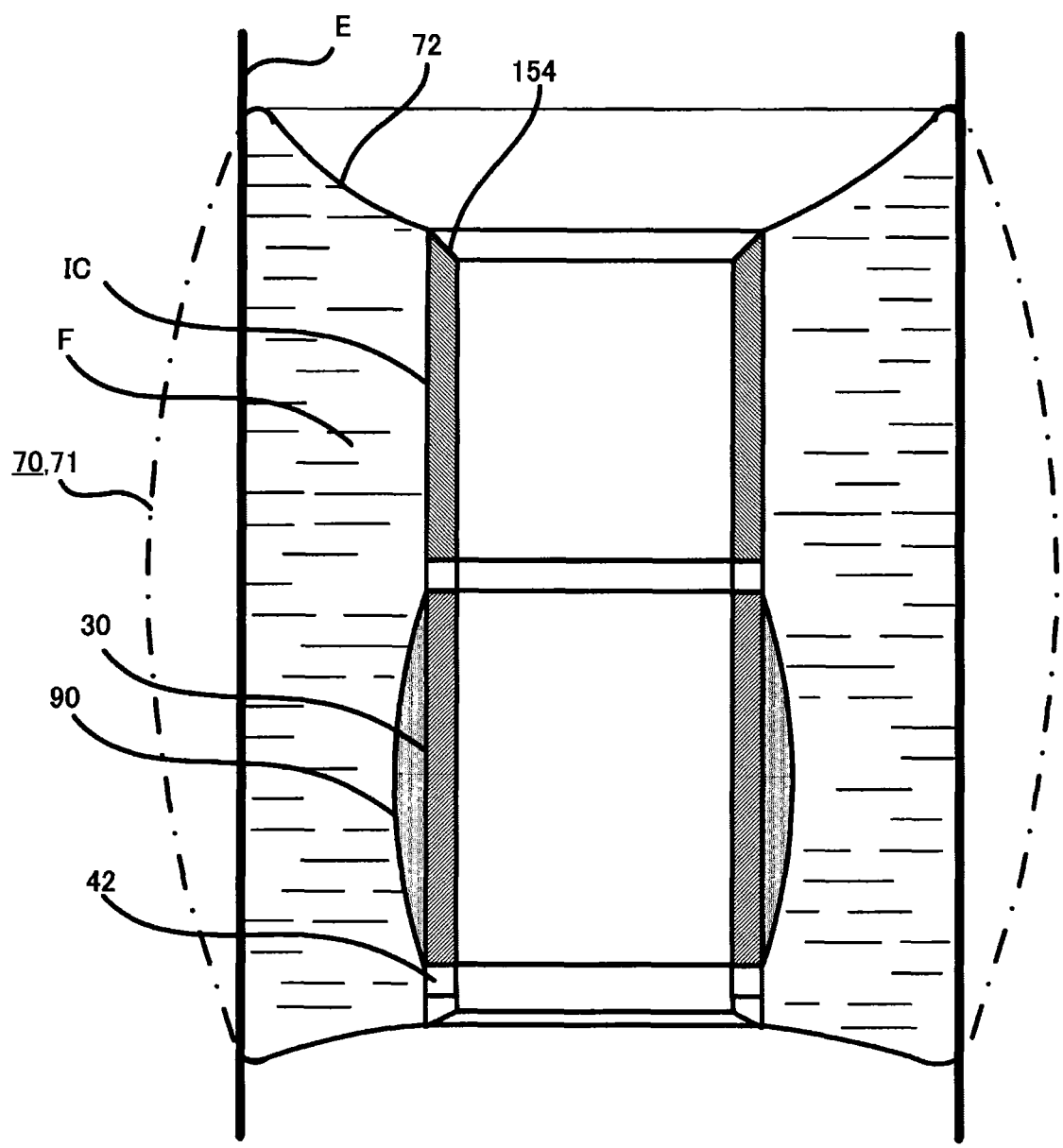
FIG. 15 is a longitudinally sectioned view of the capsule-type main body with its expansion and contraction body deflated.

Now, a second embodiment of ultrasound medical device is described 20 with reference to FIG. 14 and FIG. 15. FIG. 14 is a longitudinally sectioned view of a capsule-type main body with its expansion and contraction body 70 inflated, and FIG. 15 is a longitudinally sectioned view of the capsule-type main body with the expansion and contraction body 70 deflated.

Incidentally, the parts of the configuration of the second embodiment that are the same as those of the first embodiment are designated with the corresponding identical numbers, for leaving out description of the identical parts, and the following description mainly describes different parts in the configuration.

As shown in FIGS. 14 and 15, the support 15, the ultrasound transducers 30, the integrated circuit IC, the ultrasonic motor 42, and the acoustic lens 90 are configured in the same way as in the first embodiment.

In the first embodiment, the expansion and contraction body 70 is realized with a bag-like container 71, which is simply inflated and deflated. For this purpose, the bag-like container 71 used has a very good elasticity. The configuration is, however, not restricted to this, so the second embodiment does not depend on the superiority or inferiority in elasticity of the bag-like container 71.

FIG. 14 shows the bag-like container 71 in deflated state; and FIG. 15 shows, in solid line, the bag-like container 71 inflated in the esophagus E and, in imaginary line (dash-dot line), the bag-like container 71 inflated outside the body.

In the second embodiment, the expansion and contraction body 70 comprises a bag-like container 71 that assumes approximately identical surface areas for both inflated and deflated states. Such a bag-like container 71 has the advantage that the shape it assumes when inflated is easily recognizable. Incidentally, the liquid used to fill the bag-like container 71 for expansion is the same as that used in the first embodiment.

At the inlet of the bag-like container 71 (the opening on the top side in FIG. 15), provided is a guiding face 72, which is a long slope smoothly continuous from a slanted face 154 to the wall of the esophagus E or vice versa. Fluid food, etc. almost all passing through the esophagus E are, therefore, led from the guiding face 72 to the slanted face 154 and are readily passed through the through-hole 153, directly or indirectly.

Now, the actions of the expansion and contraction body 70 are described with reference to FIG. 14 and FIG. 15.

When the capsule-type main body 10 is inserted into the esophagus E, the bag-like container 71 is kept deflated as shown in FIG. 14. When the bag-like container 71 is deflated, wrinkles appear on the surface of the bag-like container 71, and furthermore, folds may result in part of the surface that is not absorbed in the wrinkles. Since the capsule-type main body 10 in this embodiment has the through-hole 153, which passes through in the direction of the axis of the cylindrical tube, the folds can be placed into the through-hole 153. FIG. 14 shows the folds, which are indicated with "B".

After the capsule-type main body 10 has been inserted at a predetermined location in the esophagus E, some liquid from outside the body is led through the hollow tube 23 to fill the bag-like container 71. As a result, the bag-like container 71 is inflated to adhere to the wall of the esophagus E. At this instant, the guiding face 72 expands from the slanted face 154 to the wall of the esophagus E.

While some internals of the subject P are being monitored in image, the "pulling back" of the capsule-type main body 10 is executed with the guiding hollow tube 20, for positioning.

While the capsule-type main body 10 is kept in place in the esophagus E, observation is performed. In this condition, fluid food, etc. can be passed through the through-hole 153, directly or indirectly, while the guiding face 72 facilitates the passage of the fluid food, etc.

Third Embodiment

Now, a third embodiment of ultrasound medical device is described with reference to FIG. 16, which is a cross-sectional view of a capsule-type main body with its expansion and contraction body deflated.

Incidentally, the parts of the configuration of the third embodiment that are the same as those of the first embodiment are designated with the corresponding identical numbers. By leaving out description of the identical parts, the following description mainly deals with different parts of the configuration.

In the first embodiment, the expansion and contraction body 70 is realized with a bag-like container 71 that is simply inflated and deflated. The configuration is, however, not restricted to this, so the second embodiment employs a bag-like container 71 that is folded when deflated and is expanded when inflated.

Figure 16:
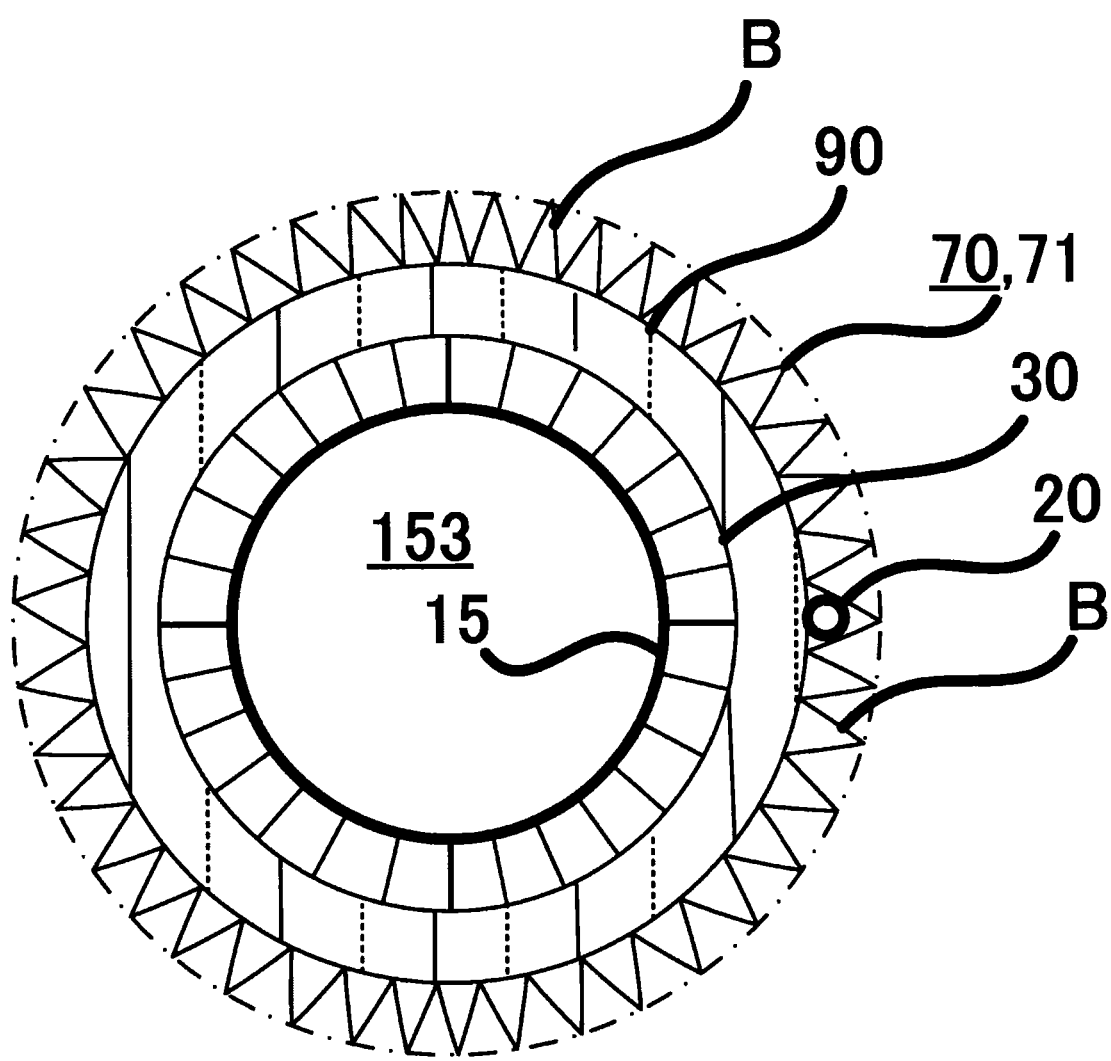
FIG. 16 is a cross-sectional view of a capsule-type main body as a third embodiment, shown with its expansion and contraction body deflated.

As shown in FIG. 16, the bag-like container 71 is provided with bellows-like folds around its peripheral surface (all-around). When the bag-like container 71 in its deflated state is supplied with liquid to fill therein, the folds are extended, and the bag-like container 71 is inflated. FIG. 16 shows the folds, which are indicated with "B".

The bag-like container 71 of the third embodiment, as is the case with the second embodiment, does not depend on the superiority or inferiority in elasticity of the bag-like container 71.

Fourth Embodiment

Figure 17:
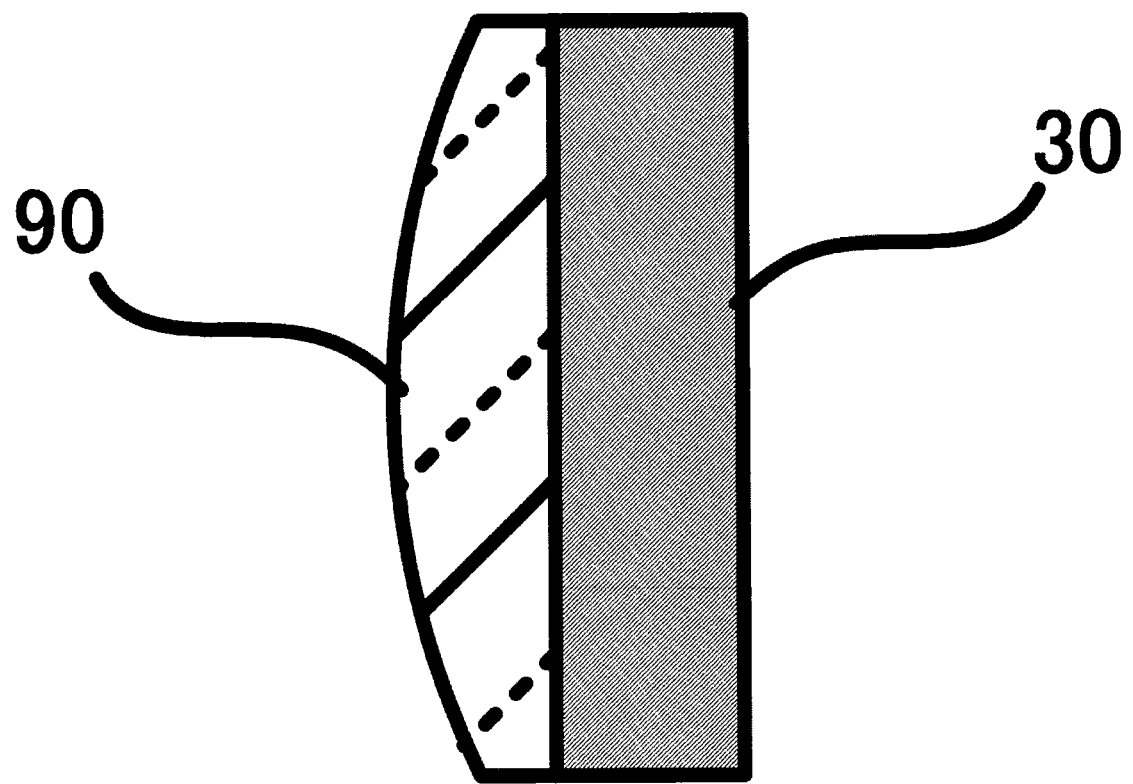
FIG. 17 is a longitudinally sectioned view showing an ultrasound transducer and an acoustic lens as a fourth embodiment.

Now, a fourth embodiment of ultrasound medical device is described with reference to FIGS. 17 and 18. FIG. 17 is a longitudinally sectioned view showing an ultrasound transducer and an acoustic lens, and FIG. 18 is a longitudinally sectioned view showing the ultrasound transducer and the acoustic lens with an offset member inserted between them.

Incidentally, the parts of the configuration of the fourth embodiment that are the same as those of the first embodiment are designated with the corresponding identical numbers, for leaving out description of the identical parts, and the following description mainly describes different parts in the configuration.

In the first embodiment, the ultrasound transducers 30 are shown with the surface (surface from which ultrasound waves are emitted) that is in the direction intersecting at a right angle with the axis of the cylindrical tube, i.e., without an elevation angle. However, the second embodiment comprises ultrasound transducers 30 that have an elevation angle. Incidentally, this elevation angle may be also referred to as "tilting angle".

Figure 18:
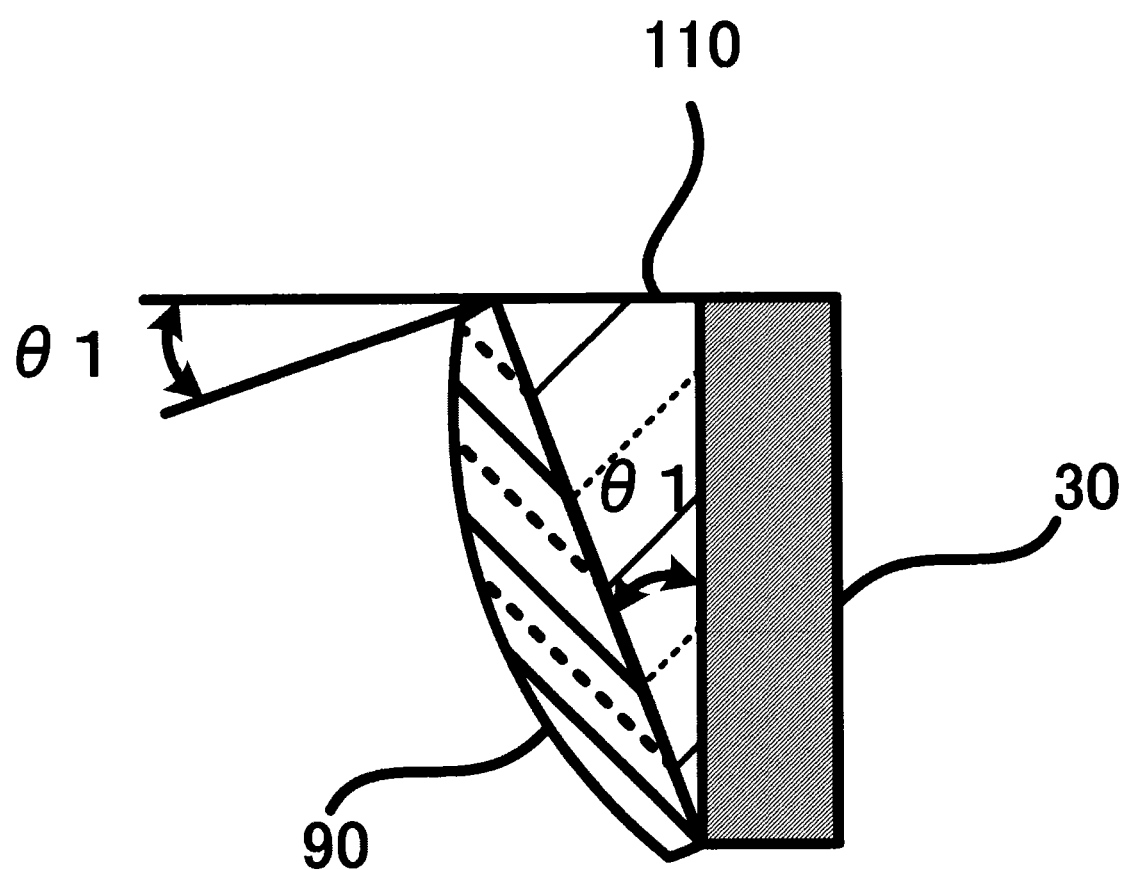
FIG. 18 is a longitudinally sectioned view showing the ultrasound transducer and the acoustic lens with an offset member inserted between them.

As shown in FIGS. 17 and 18, the configuration is such that a wedge-shaped offset member 110 is put in or put out between the ultrasound transducers 30 and the acoustic lens 90 to provide the ultrasound transducers 30 with an angle (elevation angle). The direction of the "angle" corresponds to the direction of the elevation angle (i.e., the direction of the heart) on the side looked up from the capsule-type main body 10 kept in place in the esophagus (i.e., the throat side). In FIG. 18, the elevation angle is indicated with "θ1". The elevation angle is adjustable with the angle of the wedge. If the observation object is the heart, accordingly, the capsule-type main body 10 is used with the offset member 110 preset therebetween. If the observation object is other than the heart, then the capsule-type main body 10 is used without the offset member 110, i.e., the offset member 110 is removed beforehand.

Incidentally, the means for adding an elevation angle to the ultrasound transducers 30 is not limited to the offset member 110. For example, there can be provided an air reservoir made of rubber outside the body, and it can be pressed for feeding the air. In this configuration, if the pressure is reduced, then some air returns, decreasing the elevation angle. By experimentally predetermining the relations between the feeding of the air and the elevation angle, the visualization of the amount having been fed can be used for the indication of the elevation angle. The feeder is provided with a cock, and after a predetermined elevation angle has been achieved, the cock is shut to retain the condition.

Furthermore, the means for adding an elevation angle may be columnar balloons, which are placed at two or four corners of a mechanism that is attached to the ultrasound transducers 30. Then, air is fed into the individual balloons from outside the body, thus inflating the balloons and making adjustment to achieve an arbitrary elevation angle. In stead of feeding air to the balloons, water or other liquid that is harmless to living bodies and has some viscosity may be fed to adjust and securely maintain the elevation angle.

In this way, while the capsule-type main body 10 is kept in place in the esophagus E, it is possible to change the beam angle at which the ultrasound transducers 30 emit ultrasound waves.

Fifth Embodiment

Figure 19:
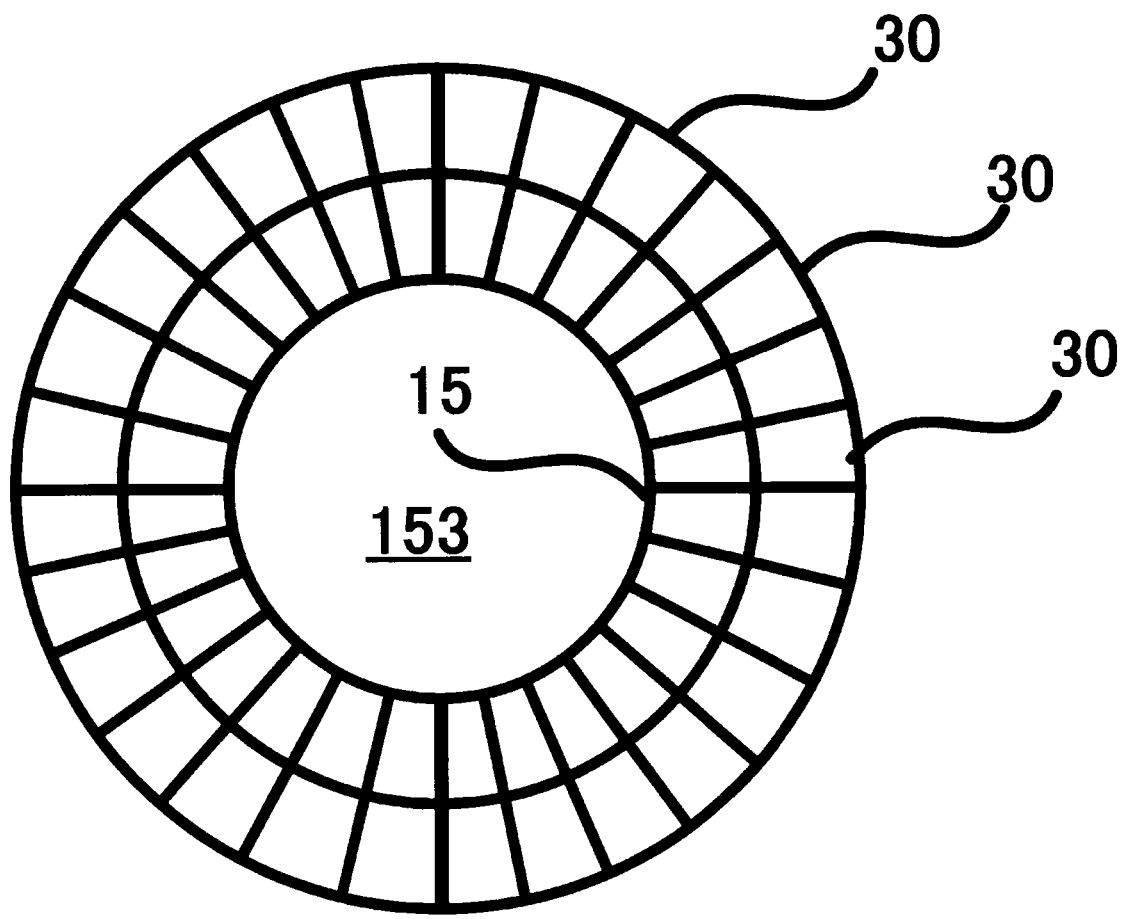
FIG. 19 is a plan view of one-dimensionally arranged ultrasound transducers as a fifth embodiment.

Now, a fifth embodiment of ultrasound medical device is described with reference to FIGS. 19 and 20. FIG. 19 is a plan view showing one-dimensionally arranged ultrasound transducers 30, and FIG. 20 is a front view showing the one-dimensionally arranged ultrasound transducers 30.

Incidentally, the parts of the configuration of the fifth embodiment that are the same as those of the first embodiment are designated with the corresponding identical numbers for leaving out description of the identical parts, and the following description mainly describes different parts in the configuration.

In the first embodiment, the ultrasound transducers 30 do not have an elevation angle. However, the fifth embodiment comprises ultrasound transducers 30 that have an elevation angle.

Figure 20:
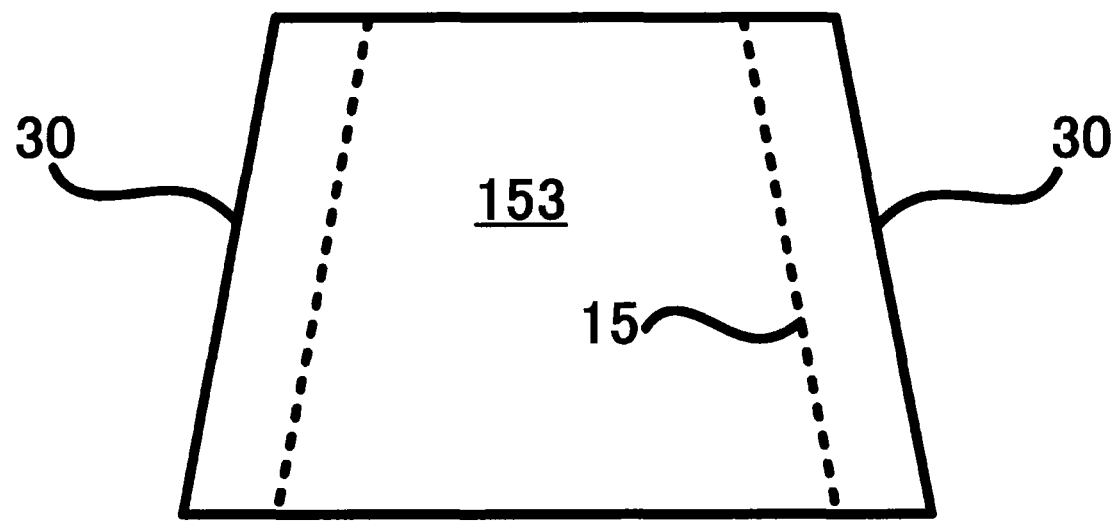
FIG. 20 is a front view of the one-dimensionally arranged ultrasound transducers.

As shown in FIGS. 19 and 20, the support 15 has a truncated circular conic shape, and a plurality of ultrasound transducers 30 are arranged circumferentially around the support 15 to endow the ultrasound transducers 30 with an elevation angle.

Now, the following describes a process of manufacturing a capsule-type main body 10 that incorporates such a support 15 and ultrasound transducers 30.

At first, a shape-memory alloy plate is so prepared that it will assume a cylindrical tube shape at temperatures lower than a predetermined temperature (e.g., 50 degrees C.), but it will assume a truncated circular conic shape with one end acquiring a smaller diameter while the other end a larger one when the plate is heated to a temperature above the predetermined temperature.

Then, at room temperature (e.g., 20 degrees C.), ultrasound transducers 30 are arranged circumferentially around the shape-memory alloy plate that is in the cylindrical tube shape. At this instant, no elevation angle is provided to the ultrasound transducers 30. The ultrasound transducers 30 in this state are then incorporated into the capsule-type main body 10. Likewise, other parts, for example, the integrated circuit IC, the expansion and contraction body 70, and the acoustic lens 90 are also incorporated into the capsule-type main body 10.

The capsule-type main body 10 is produced by the above-mentioned method.

Now, the description concerns how to use the capsule-type main body 10, which has been produced in the above-mentioned way.

The capsule-type main body 10 is inserted into the esophagus E. At the temperature of the subject P (e.g., 36 degrees C.), the ultrasound transducers 30 are not provided with any elevation angle.

After the capsule-type main body 10 is positioned in the esophagus E and ready for internal observation of the subject P, the support 15 is heated to a higher temperature (e.g., 50 degrees C.) (for example, by pouring hot water at 50 degrees), to make the support 15 transform from the cylindrical tube shape into the truncated cone shape. This action adds an elevation angle to the ultrasound transducers 30 and makes it easy to perform observation of the heart. For heating the support 15, hot water is simply led from outside the body through the hollow tube 23 into the expansion and contraction body 70. In this way, the heat of the hot water filling the expansion and contraction body 70 heats the support 15. Incidentally, if observation is to be done on other organs rather than the heart, then the support 15 should not be heated.

Sixth Embodiment

Figure 21:
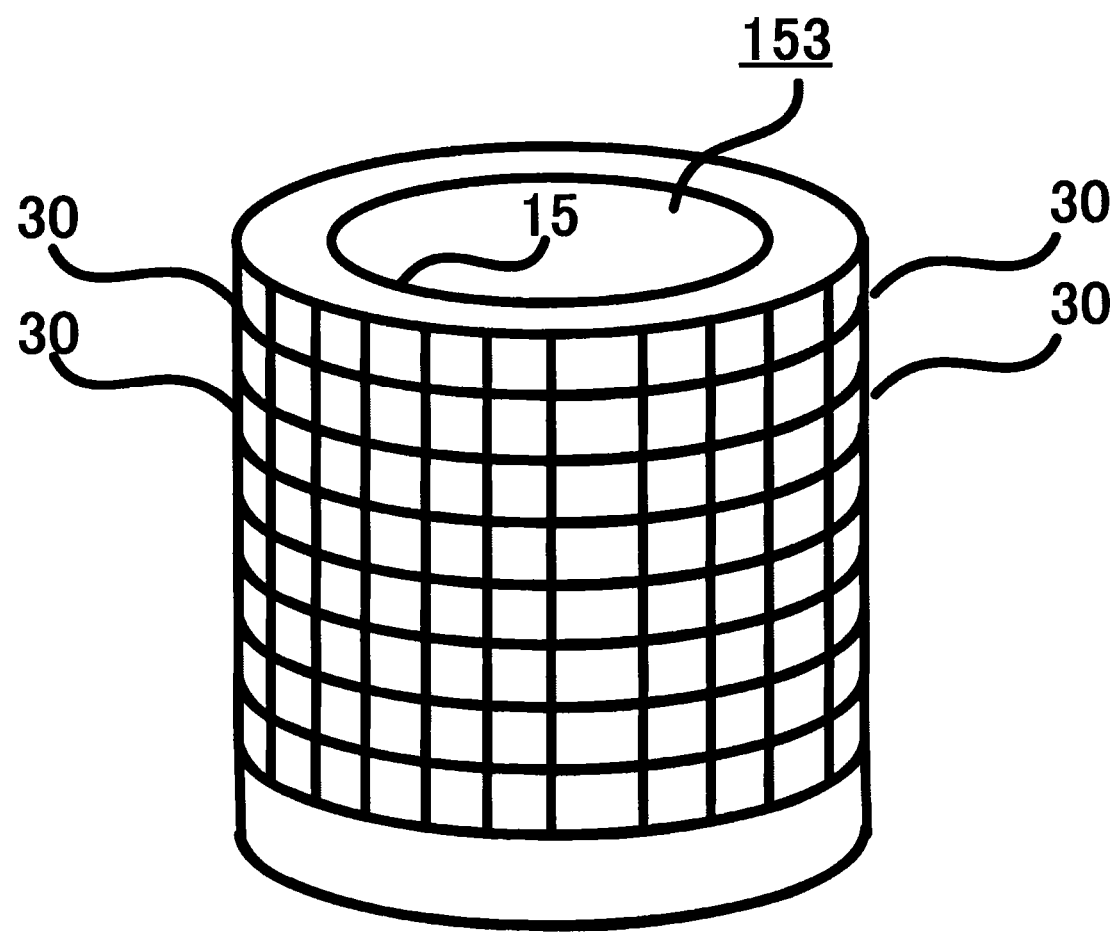
FIG. 21 is a perspective view of a plurality of ultrasound transducers arranged in two dimensions along the circumference, as a sixth embodiment.
Figure 22:
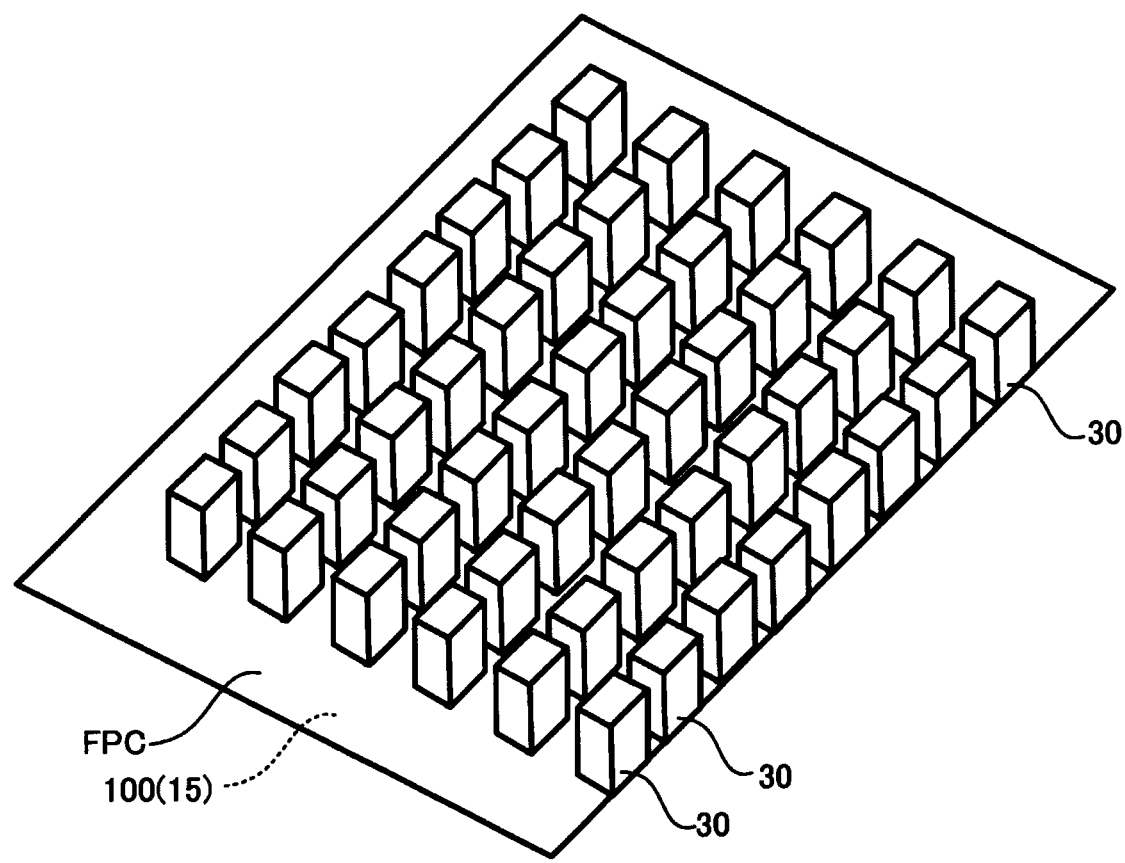
FIG. 22 is a perspective view of a plurality of ultrasound transducers arranged in two dimensions on an FPC board.

Now, a sixth embodiment of ultrasound medical device is described with reference to FIGS. 21 and 22. FIG. 21 is a perspective view showing a plurality of ultrasound transducers arranged in two dimensions along circumference, and FIG. 22 is a perspective view showing a plurality of ultrasound transducers arranged in two dimensions on an FPC board.

Incidentally, the parts of the configuration of the sixth embodiment that are the same as those of the first embodiment are designated with the corresponding identical numbers for leaving out description of the identical parts, and the following description mainly describes different parts in the configuration.

While the first embodiment comprises ultrasound transducers 30 in radial array type (refer to FIGS. 4, 5, and 6), the ultrasound transducers 30 in the sixth embodiment are arranged circumferentially around and axially along a cylindrical tube form (two-dimensional array type).

With the two-dimensional array type, only the ultrasound transducers 30 positioned within a predetermined area of all the transducers can be driven in a predetermined order for scanning the observation object such as the heart. In this case, it is not necessary to physically direct the direction of the ultrasound transducers 30 to the observation object such as the heart. Accordingly, it is not necessary to provide means for physically changing the direction of the ultrasound transducers 30, for example, the modifier 40 provided in the first embodiment. In addition, no acoustic lens 90 to constrict the ultrasonic beam is necessary.

Incidentally, the two-dimensional array type should not be limited to the ultrasound transducers 30 arranged cylindrically all around as shown in FIG. 21. It can be a two-dimensional array of a narrower field of view whose tilting mechanism is used for adjusting the field of view such that a three-dimensional image can be generated in an arbitrary position.

Now, a method of manufacturing the ultrasound transducers 30 of this type is explained with reference to FIG. 22.

As shown in FIG. 22, micro-ultrasound transducers 30 are disposed as a group in a two-dimensional array on an FPC board (subassembly).

Then, this is joined with a shape-memory alloy plate 100 to form a tubular probe. In this case, the shape-memory alloy plate 100 becomes the support 15. The shape-memory alloy plate 100 assumes a flat plate at a predetermined temperature (body temperature or at temperatures lower than, for example, 20 degrees C.) and assumes a cylindrical tube when heated above the predetermined temperature, which is the same property as applied in the first embodiment. In addition, the incorporation of such ultrasound transducers 30 into the capsule-type main body 10 is carried out in the same way as in the first embodiment.

Seventh Embodiment

Now, a seventh embodiment of ultrasound medical device is described with reference to FIGS. 23 and 24. FIG. 23 is a perspective view showing ultrasound transducers arranged in a plane outside the support, and FIG. 24 is a cross-sectional view showing the capsule-type main body with its expansion and contraction body inflated.

Incidentally, the parts of the configuration of the seventh embodiment that are the same as those of the first embodiment are designated with the corresponding identical numbers for leaving out description of the identical parts, and the following description mainly describes different parts in the configuration.

While the first embodiment comprises ultrasound transducers 30 arranged in a tubular form as a radial array type (refer to FIGS. 4, 5 and 6), the ultrasound transducers 30 in the seventh embodiment are ultrasound transducers 30 arranged in a flat plate form (one-dimensional array type).

As shown in FIG. 23, the ultrasound transducers 30 arranged in a flat plate is disposed outside a tubular support 15. The ultrasound transducers 30 are also arranged rotatable around the axis that passes through the flat plate at a right angle. In FIG. 23, the center of rotation is indicated with "Oy", and the rotational direction is indicated with an arrow.

As shown in FIG. 17, an acoustic lens 90 is attached to the surface of the flat-plate-like ultrasound transducers 30.

The ultrasound transducers 30 of this one-dimensional array are arranged to rotate around the axis of the cylindrical tube, for example, by an ultrasonic motor 42 (refer to FIG. 4). The acoustic lens 90 is so arranged that it is proximate to or in contact with the inner surface of the expansion and contraction body 70 and that the acoustic lens 90 moves along the inner surface of the expansion and contraction body 70 when the ultrasound transducers 30 are rotated by the ultrasonic motor 42 (refer to FIG. 4).

Eighth Embodiment

Now, an eighth embodiment of ultrasound medical device is described with reference to FIG. 25, which is a drawing showing ultrasound transducers arranged like a contact lens.

Incidentally, the parts of the configuration of the eighth embodiment that are the same as those of the first embodiment are designated with the corresponding identical numbers for leaving out description of the identical parts, and the following description mainly describes different parts in the configuration.

While the first embodiment comprises ultrasound transducers 30 arranged in a tubular form as a radial array type, the eighth embodiment comprises ultrasound transducers arranged like a contact lens.

Figure 25:
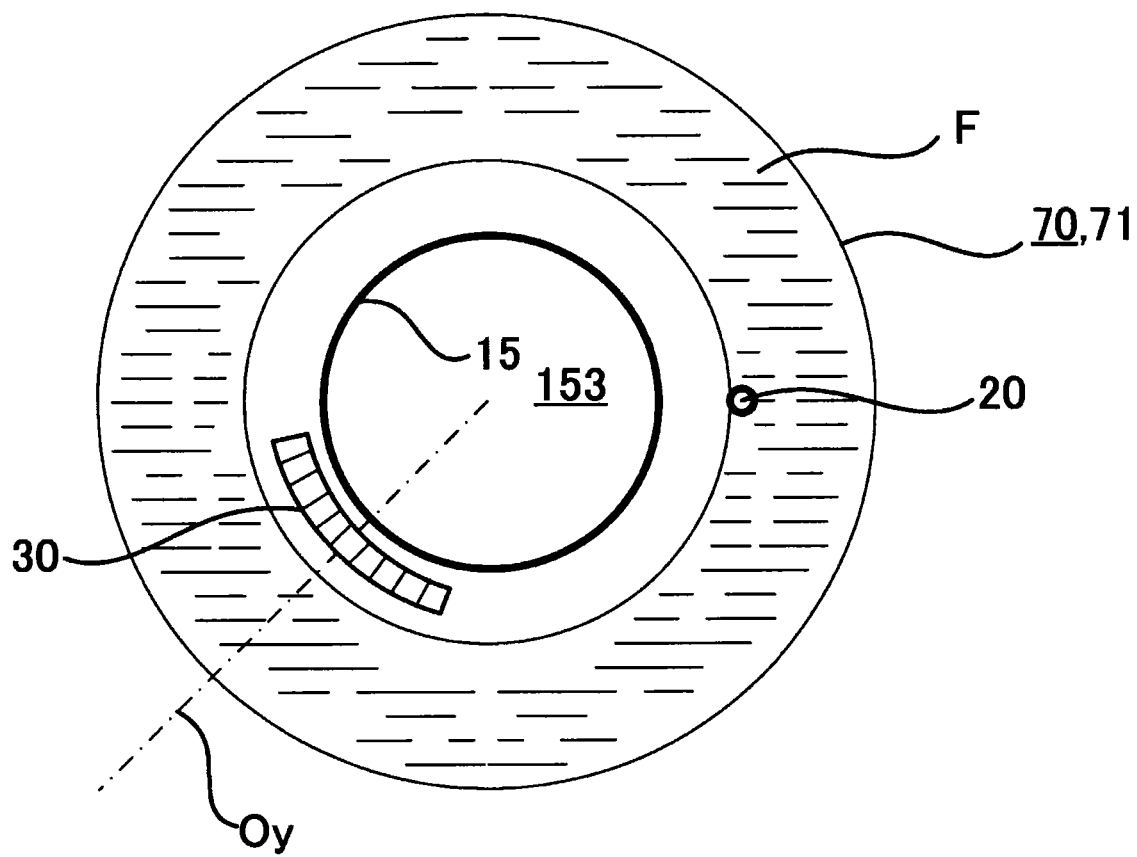
FIG. 25 is a drawing showing ultrasound transducers arranged like a contact-lens, as an eighth embodiment.

As shown in FIG. 25, the ultrasound transducers 30 are arranged like a contact lens outside a tubular support 15. In this case, the ultrasound transducers 30 are arranged rotatable around the central axis of the contact lens. In FIG. 25, the central axis is indicated with "Oy".

With the ultrasound transducers 30 arranged like a contact lens, the installation space for the ultrasound transducers 30 (the gap between the support 15 and the expansion and contraction body 70) may be made narrower than that in the seventh embodiment shown in FIG. 24. As a result, the diameter of the through-hole 153 can be increased to a degree that corresponds to the space saved, which is advantageous for passing fluid food through.

Ninth Embodiment

Figure 26:
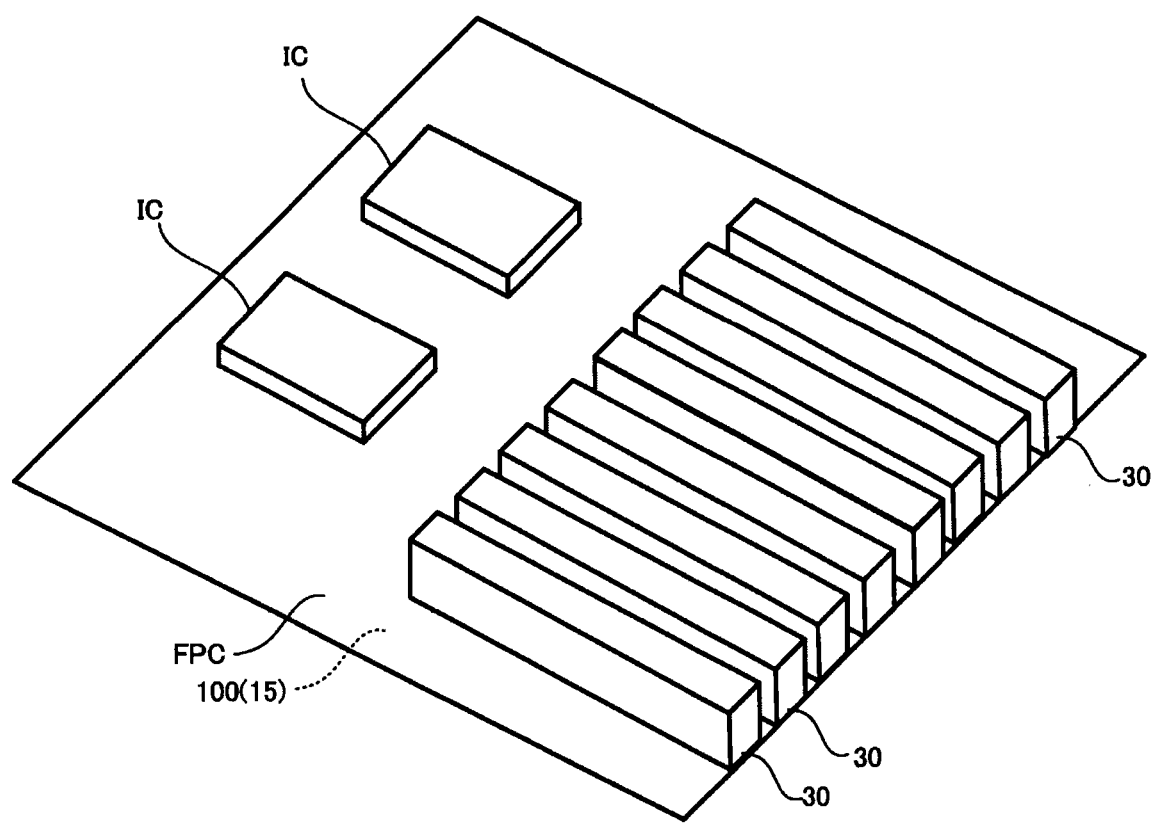
FIG. 26 is a perspective view showing ultrasound transducers, etc. provided on an FPC board, as a ninth embodiment.

Now, a ninth embodiment of ultrasound medical device is described with reference to FIG. 26, which is a perspective view showing ultrasound transducers, etc. mounted on an FPC board.

Incidentally, the parts of the configuration of the ninth embodiment that are the same as those of the first embodiment are designated with the corresponding identical numbers for leaving out description of the identical parts, and the following description mainly describes different parts in the configuration.

In the production of the capsule-type main body 10, while the first embodiment comprises strip-like ultrasound transducers 30 that are fixed on an FPC, the ninth embodiment comprises integrated circuits IC in addition to the ultrasound transducers 30 that are fixed (subassembly).

This is then joined with a shape-memory alloy plate 100 to configure a tubular probe in the same way as in the first embodiment. In this way, the ultrasound transducers 30 and the integrated circuits IC can be fixed at once in the production.

(Mounting of an Electronic Circuit)

Figure 27:
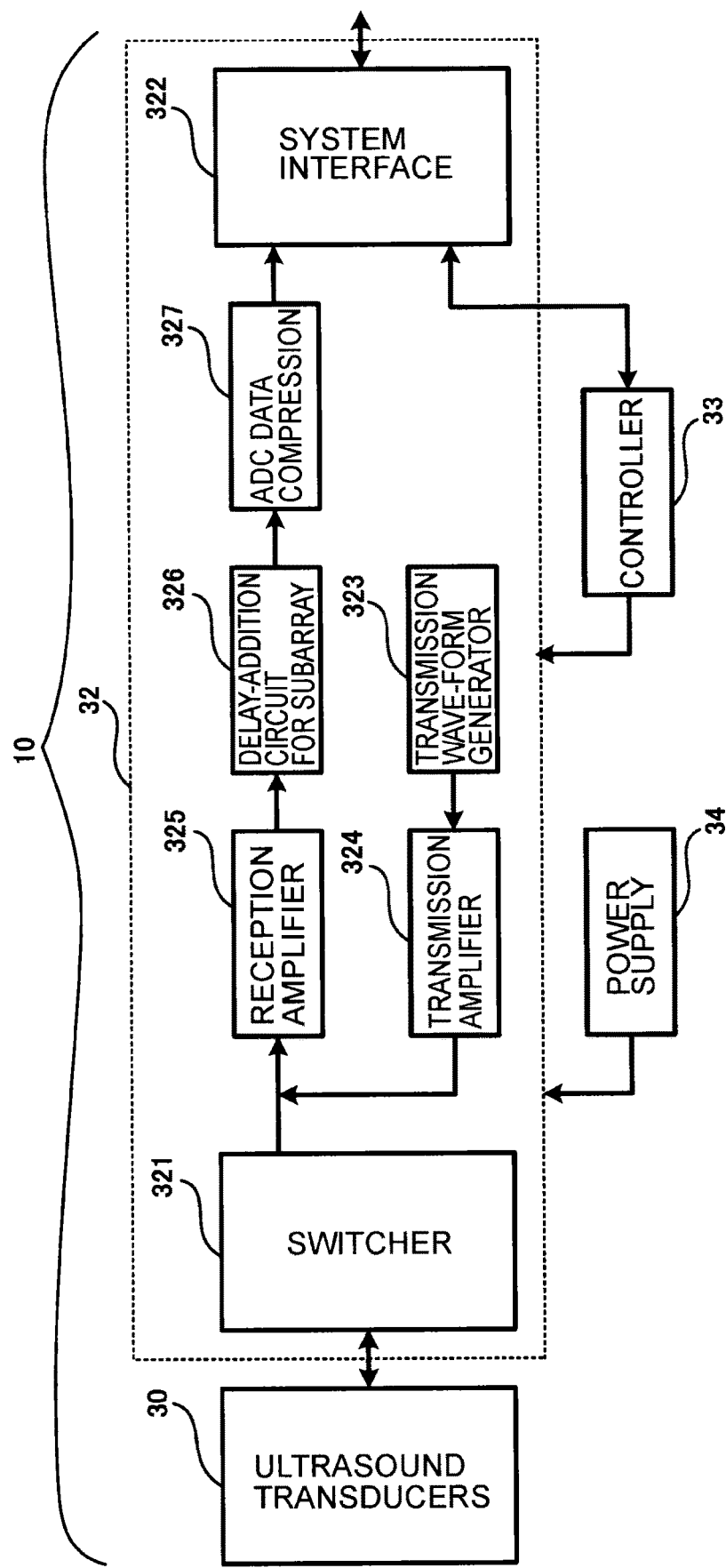
FIG. 27 is a block diagram of an electronic circuit that is provided in the capsule-type main body.

Now, the description concerns the mounting of an electronic circuit with reference to FIGS. 13 and 27.

FIG. 27 is a block diagram showing an electronic circuit for the ultrasound transducers 30 incorporated in the capsule-type main body 10.

As shown in FIG. 27, a switcher 321 is used for selection of a desired element group. Control data are received through a system interface 322, and based on the data, transmission wave-form signals are generated with necessary delays (transmission wave-form generator 323). Then, the transmission wave-form signals are amplified by a transmission amplifier 324 to drive the ultrasound transducers 30. They may be pulses. Ultrasound waves are emitted to the inside of a living body, and they are reflected and scattered in the body, and some are received by the transducers. The signals are amplified by a reception amplifier 325, and signals from nearby elements are delay-addition processed to create partial beam signals (delay-addition circuit 326). In this case, if subarray size is assumed to be, for example, 4 elements, then the number of signals decreases to a quarter. Furthermore, if these subarray output signals are analog-to-digital converted, then data filtered correspondingly with the bandwidth of the ultrasonic signals are culled to further reduce the signals (ADC327). For example, even if the analog to digital conversion is executed at 40 Msps, as long as the bandwidth of the ultrasonic signals is about 5 MHz, the doubling of the sampling frequency to 10 MHz can reduce the number of signals to about a quarter. In the case where data width is one byte and the number of elements is 64, 320 Mbps per channel add up to 20 Gbps. However, the above-mentioned data reduction reduces the rate to 1.28 (=20/16) Gbps. A high speed serial transfer system, which has been developed in recent years can sufficiently transfer the data at such a rate. Of course, any general-purpose data compression technique may be applied to reduce the frame rate. If the data volume is reduced in this way, even a current radio-communication system is effective for data transfer. As for power supply, the means for supplying power can be a cable provided in the string or a battery.

In addition, information can be transferred in analog signals as are. In this case, a coaxial cable can be used even for a case of 16 (=64/4) cables, each having a diameter of 0.2 to 0.3 mm, making a total cable diameter of 1 to 1.5 mm.

Incidentally, in the above-mentioned embodiments, the backing material comprises a materiel that has an acoustic impedance lower than that of the piezoelectric material used. However, embodiments are not limited to this.

The following description concerns a method of manufacturing a probe that uses a backing material with an acoustic impedance higher than that of the piezoelectric material.

At first, ultrasound transducers 30 are fixed on an FPC, and the FPC is joined to a shape-memory alloy. Then, ultrasound transducers 30 are configured using a flexible piezoelectric material such as polyvinylidene fluoride (PVDF), and they are joined to a shape-memory alloy plate.

Then, in the case where the piezoelectric material has as low an acoustic impedance as the PVDF, the shape-memory alloy plate 100 itself is used as backing material. Incidentally, if necessary, a backing material can be placed between the piezoelectric material and the shape-memory alloy plate 100. Since it places an additional thickness, however, it is preferable that the shape-memory alloy plate itself be used as backing material for the purpose of miniaturization.

Incidentally, if the piezoelectric material is ceramic, then the shape-memory alloy plate 100 made of tungsten, which has an acoustic impedance higher than that of the ceramic, may be used as backing material.

The embodiments of the present invention were set forth; however, the embodiments described above were presented as examples and are not intended to limit the range of the invention. These new embodiments may be carried out in various other configurations, and various abbreviations, replacements, and changes may be made in a range not departing from the summary of the invention. These embodiments and deformations thereof are included in the range and summary of the invention and included in the invention described in the range of patent claims as well as the range of the equivalent thereof.

What is claimed is:

1. An ultrasound medical device comprising:
   ultrasound transducers;
   a capsule-type main body configured to incorporate the ultrasound transducers, so that the ultrasound transducers within the capsule-type main body, which is configured to be inserted in a tubular body part of a subject, send ultrasound waves to an organ as an observation object in the subject's interiors and receive reflected waves;
   a support incorporated in the capsule-type main body and to have a form of a tube with a through-hole axially passing through the tube to let fluid food through, the tube having first and second ends with a slanted face formed at each end thereof to be smoothly continuous to the through-hole;
   an ultrasonic motor that is disposed at one end of the support and configured to cause the ultrasound transducers to make a rotational movement around a longitudinal axis of the support and relative to the support; and
   a bag-like container configured to be filled with heated fluid via a hollow tube to heat the support, wherein
   the ultrasound transducers are arranged external to the tube;
   the support is made of a shape-memory alloy having the tube form at temperatures lower than a predetermined temperature while having a truncated cone form whose one end has a smaller diameter than the other end when heated to a temperature higher than the predetermined temperature; and
   when the support is heated to a temperature higher than the predetermined temperature, the support modifies a beam angle of ultrasound waves emitted by the ultrasound transducers.

2. The ultrasound medical device according to claim 1, wherein the through-hole is a bore to let the fluid food through.

3. The ultrasound medical device according to claim 1, wherein the through-hole is a bore also to let a transnasal endoscope through.

4. The ultrasound medical device according to claim 3, further comprising a guiding hollow tube configured to be attached to the capsule-type main body by a leading end thereof and to be insertable into the tubular body part, wherein
the guiding hollow tube comprises a hollow tube, which is used for feeding a liquid into and discharging the liquid from an expansion and contraction body, the hollow tube is a region of the guiding hollow tube.

5. The ultrasound medical device according to claim 1, further comprising:
an acoustic lens and a wedge-shaped offset member,
wherein a beam angle of ultrasound waves emitted by the ultrasound transducers is modified by inserting or removing the offset member between the acoustic lens and the ultrasound transducers.

6. The ultrasound medical device according to claim 1, wherein
the ultrasound transducers are made of a piezoelectric material that has an acoustic impedance lower than that of the shape-memory alloy; and
the shape-memory alloy is used as backing material.

7. The ultrasound medical device according to claim 1, wherein
the ultrasound transducers have a tubular form and are controlled by a controller provided in an integrated circuit; and
the integrated circuit has a same tubular form as the ultrasound transducers and is coaxially disposed adjacent to the ultrasound transducers.

8. An ultrasound medical device comprising:
ultrasound transducers;
a capsule-type main body configured to incorporate ultrasound transducers, so that the ultrasound transducers within the capsule-type main body, which is configured to be inserted in a tubular body part of a subject, send ultrasound waves to an organ as an observation object in the subject's interiors and receive reflected waves;
a support incorporated in the capsule-type main body and to have a form of a tube, along an outer circumference of which the ultrasound transducers are arranged, the tube having a through-hole axially passing through to let fluid food through for maintaining functions of the tubular body part after the capsule-type main body has been inserted into the tubular body part and having first and second ends with a slanted face formed at each end thereof to be smoothly continuous to the through-hole;
a bag-like container configured to be disposed to cover the ultrasound transducers externally, which is configured to be inflated to bring the bag-like container into contact with a wall of the tubular body part; and
an ultrasonic motor that is disposed at one end of the support and configured to cause the ultrasound transducers to make a rotational movement around a longitudinal axis of the support and relative to the support, wherein
the bag-like container is configured to be filled with heated fluid via a hollow tube to heat the support;
the support is made of a shape-memory alloy having the tube form at temperatures lower than a predetermined temperature while having a truncated cone form whose one end has a smaller diameter than the other end, when heated to a temperature higher than the predetermined temperature; and
when the support is heated to a temperature higher than the predetermined temperature, the support modifies a beam angle of ultrasound waves emitted by the ultrasound transducers.

9. The ultrasound medical device according to claim 8, further comprising a guiding hollow tube configured to be attached to the capsule-type main body by a leading end thereof and to be insertable into the tubular body part, wherein
the guiding hollow tube comprises a hollow tube, which is used for feeding a liquid into and discharging the liquid from the bag-like container, the hollow tube is a region of the guiding hollow tube.

10. The ultrasound medical device according to claim 8, wherein the through-hole is a bore to let the fluid food through.

11. The ultrasound medical device according to claim 8, wherein the through-hole is a bore also to let a transnasal endoscope through.

12. The ultrasound medical device according to claim 8, further comprising:
an acoustic lens and a wedge-shaped offset member,
wherein a beam angle of ultrasound waves emitted by the ultrasound transducers is modified by inserting or removing the offset member between the acoustic lens and the ultrasound transducers.

13. The ultrasound medical device according to 8, wherein
the ultrasound transducers have a tubular form and are controlled by a controller provided in an integrated circuit; and
the integrated circuit has a same tubular form as the ultrasound transducers and is coaxially disposed above the ultrasound transducers.

14. An ultrasound diagnostic imaging device comprising:
an ultrasound medical device; and
an external device, wherein
the ultrasound medical device includes:
ultrasound transducers;
a capsule-type main body configured to incorporate the ultrasound transducers;
a support incorporated in the capsule-type main body and to have a form of a tube with a through-hole axially passing through the tube to let fluid food through, the tube having first and second ends with a slanted face formed at each end thereof to be smoothly continuous to the through-hole;
an ultrasonic motor that is disposed at one end of the support and configured to cause the ultrasound transducers to make a rotational movement around a longitudinal axis of the support and relative to the support;
a bag-like container configured to be filled with heated fluid via a hollow tube to heat the support; and
a signal line that is for transmitting and receiving signals between the external device and the capsule-type main body,
the support is made of a shape-memory alloy having the tube form at temperatures lower than a predetermined temperature while having a truncated cone form whose one end has a smaller diameter than the other end when heated to a temperature higher than the predetermined temperature;

when the support is heated to a temperature higher than the predetermined temperature, the support modifies a beam angle of ultrasound waves emitted by the ultrasound transducers;

the ultrasound transducers are arranged external to the tube;

the ultrasound medical device is configured to send ultrasound waves from the ultrasound transducers in the capsule-type main body, which is configured to be inserted in a tubular body part of a subject, to an organ as an observation object in the subject's interiors and receive reflected waves;

the capsule-type main body transmits signals that are generated from the reflected waves to the external device via the signal line; and the external device includes:
  a display; and
  processing circuitry configured to receive the signals from the capsule-type main body and process the signals to create and display ultrasound images of interior body parts of the subject on the display.

15. An ultrasound diagnostic imaging device comprising:
an ultrasound medical device; and
an external device, wherein
the ultrasound medical device includes:
  ultrasound transducers;
  a capsule-type main body configured to incorporate the ultrasound transducers;
  a support incorporated in the capsule-type main body and to have a form of a tube, along an outer circumference of which the ultrasound transducers are arranged, the tube having a through-hole axially passing through to let fluid food through for maintaining functions of a tubular body part of a subject after the capsule-type main body has been inserted into the tubular body part and having first and second ends with a slanted face formed at each end thereof to be smoothly continuous to the through-hole;
  a bag-like container configured to be disposed to cover the ultrasound transducers externally, which is inflated to bring the bag-like container into contact with a wall of the tubular body part;
  an ultrasonic motor that is disposed at one end of the support and configured to cause the ultrasound transducers to make a rotational movement around a longitudinal axis of the support and relative to the support; and
  a signal line that is for transmitting and receiving signals between the external device and the capsule-type main body, the ultrasound medical device is configured to send ultrasound waves from the ultrasound transducers in the capsule-type main body, which is configured to be inserted in the tubular body part of the subject, to an organ as an observation object in the subject's interiors and receive reflected waves;

the capsule-type main body transmits signals that are generated from the reflected waves to the external device via the signal line;

the bag-like container is configured to be filled with heated fluid via a hollow tube to heat the support;

the support is made of a shape-memory alloy having the tube form at temperatures lower than a predetermined temperature while having a truncated cone form whose one end has a smaller diameter than the other end, when heated to a temperature higher than the predetermined temperature;

when the support is heated to a temperature higher than the predetermined temperature, the support modifies a beam angle of ultrasound waves emitted by the ultrasound transducers; and the external device includes:
  a display; and
  processing circuitry configured to receive the signals from the capsule-type main body and the signals to create and display ultrasound images of interior body parts of the subject on the display.

\* \* \* \* \*